(12) United States Patent
Abdou

(10) Patent No.: US 8,845,688 B2
(45) Date of Patent: Sep. 30, 2014

(54) DEVICES AND METHODS FOR INTER-VERTEBRAL ORTHOPEDIC DEVICE PLACEMENT

(76) Inventor: Samy Abdou, San Diego, CA (US)

(*) Notice: Subject to any disclaimer, the term of this patent is extended or adjusted under 35 U.S.C. 154(b) by 286 days.

(21) Appl. No.: 12/779,839

(22) Filed: May 13, 2010

(65) Prior Publication Data

US 2010/0318128 A1    Dec. 16, 2010

Related U.S. Application Data

(63) Continuation of application No. 11/613,146, filed on Dec. 19, 2006, now Pat. No. 8,002,802.

(60) Provisional application No. 60/751,509, filed on Dec. 19, 2005, provisional application No. 60/763,411, filed on Jan. 30, 2006, provisional application No. 60/792,378, filed on Apr. 14, 2006, provisional application No. 60/815,296, filed on Jun. 20, 2006, provisional application No. 60/815,956, filed on Jun. 24, 2006, provisional application No. 60/834,209, filed on Jul. 27, 2006.

(51) Int. Cl.
    *A61B 17/70*    (2006.01)
    *A61B 17/02*    (2006.01)

(52) U.S. Cl.
    CPC ..... *A61B 17/7062* (2013.01); *A61B 2017/0256* (2013.01); *A61B 17/7065* (2013.01)
    USPC .......................................... 606/248; 606/249

(58) Field of Classification Search
    CPC ........... A61B 17/7068; A61B 17/7062; A61B 17/7067

USPC .................................................. 606/248, 249
See application file for complete search history.

(56) References Cited

U.S. PATENT DOCUMENTS

| 2,774,350 A | 12/1956 | Cleveland |
| 3,865,105 A | 2/1975 | Lode |
| 4,611,582 A | 9/1986 | Duff |
| 5,011,484 A | 4/1991 | Breard |
| 5,234,431 A | 8/1993 | Keller |
| 5,250,055 A | 10/1993 | Moore et al. |

(Continued)

FOREIGN PATENT DOCUMENTS

| EP | 418387 | 3/1991 |
| FR | 2813782 | 3/2002 |

(Continued)

OTHER PUBLICATIONS

Asazuma et al. "Intersegmental spinal flexibility with lumbosacral instrumentation. An in vitro biomechanical investigation" *Spine* Nov. 1990;15(11):1153-8.

(Continued)

*Primary Examiner* — Jerry Cumberledge
(74) *Attorney, Agent, or Firm* — Gazdzinsku & Associates, PC

(57) ABSTRACT

A spinal implant device includes a spacer region and an attachment region. The spacer region is adapted to be positioned between first and second spinous processes of first and second vertebral bodies to limit movement of the first spinous process and the second spinous process toward one another. The attachment region attaches to the first spinous process via a fastener that extends substantially along a long axis of the spinous process.

12 Claims, 35 Drawing Sheets

(56) References Cited

U.S. PATENT DOCUMENTS

| | | | |
|---|---|---|---|
| 5,261,910 A | 11/1993 | Warden et al. | |
| 5,304,178 A | 4/1994 | Stahurski | |
| 5,413,576 A | 5/1995 | Rivard | |
| 5,484,437 A | 1/1996 | Michelson | |
| 5,496,318 A | 3/1996 | Howland et al. | |
| 5,558,674 A | 9/1996 | Heggeness et al. | |
| 5,609,634 A | 3/1997 | Voydeville | |
| 5,645,599 A * | 7/1997 | Samani | 623/17.16 |
| 5,672,175 A | 9/1997 | Martin | |
| 5,725,582 A | 3/1998 | Bevan et al. | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,226,548 B1 | 5/2001 | Foley | |
| 6,312,431 B1 | 11/2001 | Asfora | |
| 6,332,882 B1 | 12/2001 | Zucherman et al. | |
| 6,379,355 B1 | 4/2002 | Zucherman et al. | |
| 6,402,750 B1 | 6/2002 | Atkinson et al. | |
| 6,419,676 B1 | 7/2002 | Zucherman et al. | |
| 6,419,677 B2 | 7/2002 | Zucherman et al. | |
| 6,440,169 B1 | 8/2002 | Elberg et al. | |
| 6,451,019 B1 | 9/2002 | Zucherman et al. | |
| 6,451,020 B1 | 9/2002 | Zucherman et al. | |
| 6,478,796 B2 | 11/2002 | Zucherman et al. | |
| 6,514,256 B2 | 2/2003 | Zucherman et al. | |
| 6,582,433 B2 * | 6/2003 | Yun | 606/249 |
| 6,665,555 B2 | 12/2003 | Henderson et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,719,795 B1 * | 4/2004 | Cornwall et al. | 623/17.11 |
| 6,733,534 B2 | 5/2004 | Sherman | |
| 6,743,257 B2 | 6/2004 | Castro | |
| 6,761,720 B1 | 7/2004 | Senegas | |
| 7,070,598 B2 | 7/2006 | Lim et al. | |
| 7,087,083 B2 | 8/2006 | Pasquet et al. | |
| 7,101,375 B2 | 9/2006 | Zucherman et al. | |
| 7,163,558 B2 | 1/2007 | Senegas et al. | |
| 7,201,751 B2 | 4/2007 | Zucherman et al. | |
| 7,306,628 B2 | 12/2007 | Zucherman et al. | |
| 7,335,203 B2 * | 2/2008 | Winslow et al. | 606/249 |
| 7,578,849 B2 * | 8/2009 | Trieu | 623/17.15 |
| 7,837,688 B2 * | 11/2010 | Boyer et al. | 606/86 A |
| 8,066,742 B2 * | 11/2011 | Anderson et al. | 606/249 |
| 2002/0147449 A1 | 10/2002 | Yun | |
| 2003/0040746 A1 | 2/2003 | Mitchell et al. | |
| 2003/0045935 A1 * | 3/2003 | Angelucci et al. | 623/17.11 |
| 2004/0019263 A1 | 1/2004 | Jutras et al. | |
| 2004/0106995 A1 | 6/2004 | Le Couedic et al. | |
| 2004/0204713 A1 | 10/2004 | Abdou | |
| 2004/0249377 A1 | 12/2004 | Kaes et al. | |
| 2004/0249379 A1 | 12/2004 | Winslow et al. | |
| 2005/0021040 A1 | 1/2005 | Bertagnoli | |
| 2005/0033434 A1 | 2/2005 | Berry | |
| 2005/0159813 A1 | 7/2005 | Molz | |
| 2005/0165398 A1 | 7/2005 | Reiley | |
| 2005/0203512 A1 | 9/2005 | Hawkins et al. | |
| 2005/0203533 A1 | 9/2005 | Ferguson et al. | |
| 2005/0203624 A1 | 9/2005 | Serhan et al. | |
| 2005/0283245 A1 | 12/2005 | Gordon et al. | |
| 2006/0036246 A1 * | 2/2006 | Carl et al. | 606/61 |
| 2006/0084977 A1 | 4/2006 | Lieberman | |
| 2006/0195102 A1 | 8/2006 | Malandain | |
| 2006/0235403 A1 * | 10/2006 | Blain | 606/69 |
| 2006/0235532 A1 | 10/2006 | Meunier | |
| 2006/0241601 A1 * | 10/2006 | Trautwein et al. | 606/61 |
| 2006/0247634 A1 | 11/2006 | Warner | |
| 2006/0293662 A1 | 12/2006 | Boyer, II et al. | |
| 2007/0093823 A1 * | 4/2007 | Booth et al. | 606/61 |
| 2007/0093825 A1 | 4/2007 | Ferree | |
| 2007/0106298 A1 | 5/2007 | Carli et al. | |
| 2007/0162000 A1 | 7/2007 | Perkins | |
| 2007/0162001 A1 | 7/2007 | Chin | |
| 2007/0191834 A1 | 8/2007 | Brumeau et al. | |
| 2007/0233077 A1 | 10/2007 | Khalili | |
| 2007/0233083 A1 | 10/2007 | Abdou | |
| 2007/0233084 A1 | 10/2007 | Betz et al. | |
| 2008/0027545 A1 | 1/2008 | Zucherman | |
| 2008/0108993 A1 | 5/2008 | Bennett et al. | |
| 2012/0296377 A1 * | 11/2012 | Ferree et al. | 606/249 |

FOREIGN PATENT DOCUMENTS

| | | |
|---|---|---|
| WO | WO 99/21500 | 5/1999 |
| WO | WO 02/051326 | 7/2002 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |
| WO | WO 2007/075843 | 7/2007 |

OTHER PUBLICATIONS

Branch et al. "Posterior lumbar interbody fusion with the keystone graft: technique and results" *Surg Neurol* May 1987;27(5):449-54.

Chiba et al. "Short-segment pedicle instrumentation. Biomechanical analysis of supplemental hook fixation" *Spine* Feb. 1, 1996;21(3):288-94.

Cobo et al. "Predictors of outcome after decompressive lumbar surgery and instrumented posterolateral fusion" *Eur Spine J* Feb. 5, 2010; [Epub ahead of print].

Dawson et al. "Intertransverse process lumbar arthrodesis with autogenous bone graft" *Clin Orthop Relat Res* Jan.-Feb. 1981;(154):90-6.

Dove J "Internal fixation of the lumbar spine. The Hartshill rectangle" *Clin Orthop Relat Res* Feb. 1986;(203):135-40.

Gill GG "Long-term follow-up evaluation of a few patients with spondylolisthesis treated by excision of the loose lamina with decompression of the nerve roots without spinal fusion" *Clin Orthop Relat Res* Jan.-Feb. 1984;(182):215-9.

Krag et al. "An internal fixator for posterior application to short segments of the thoracic, lumbar, or lumbosacral spine. Design and testing" *Clin Orthop Relat Res* Feb. 1986;(203):75-98.

Lin PM "Internal decompression for multiple levels of lumbar spinal stenosis: a technical note" *Neurosurgery* Oct. 1982;11(4):546-9.

Lorenz et al. "A comparison of single-level fusions with and without hardware" *Spine* Aug. 1991;16(8 Suppl):S455-8.

Luque ER "Segmental spinal instrumentation of the lumbar spine" *Clin Orthop Relat Res* Feb. 1986;(203):126-34.

Stambough et al. "Instrumented one and two level posterolateral fusions with recombinant human bone morphogenetic protein-2 and allograft: a computed tomography study" *Spine* Jan. 1, 2010;35(1):124-9.

Wang et al. "Comparison of CD Horizon Spire spinous process plate stabilization and pedicle screw fixation after anterior lumbar interbody fusion. Invited submission from the Joint Section Meeting on Disorders of the Spine and Peripheral Nerves Mar. 2005" *J Neurosurg Spine* Feb. 2006;4(2):132-6.

Wang et al. "SPIRE spinous process stabilization plate: biomechanical evaluation of a novel technology. Invited submission from the Joint Section Meeting on Disorders of the Spine and Peripheral Nerves, Mar. 2005" *J Neurosurg Spine* Feb. 2006;4(2):160-4.

\* cited by examiner

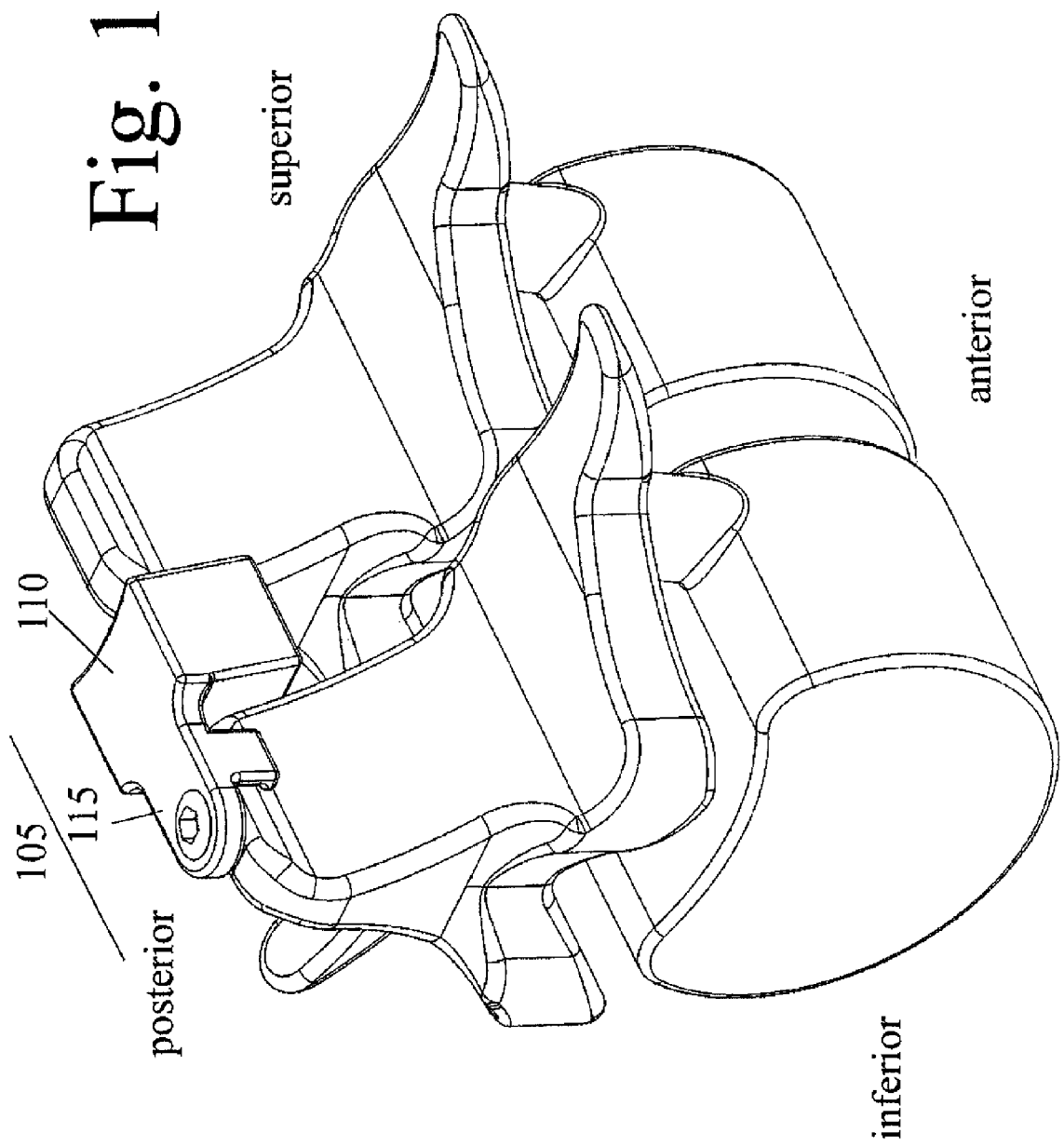

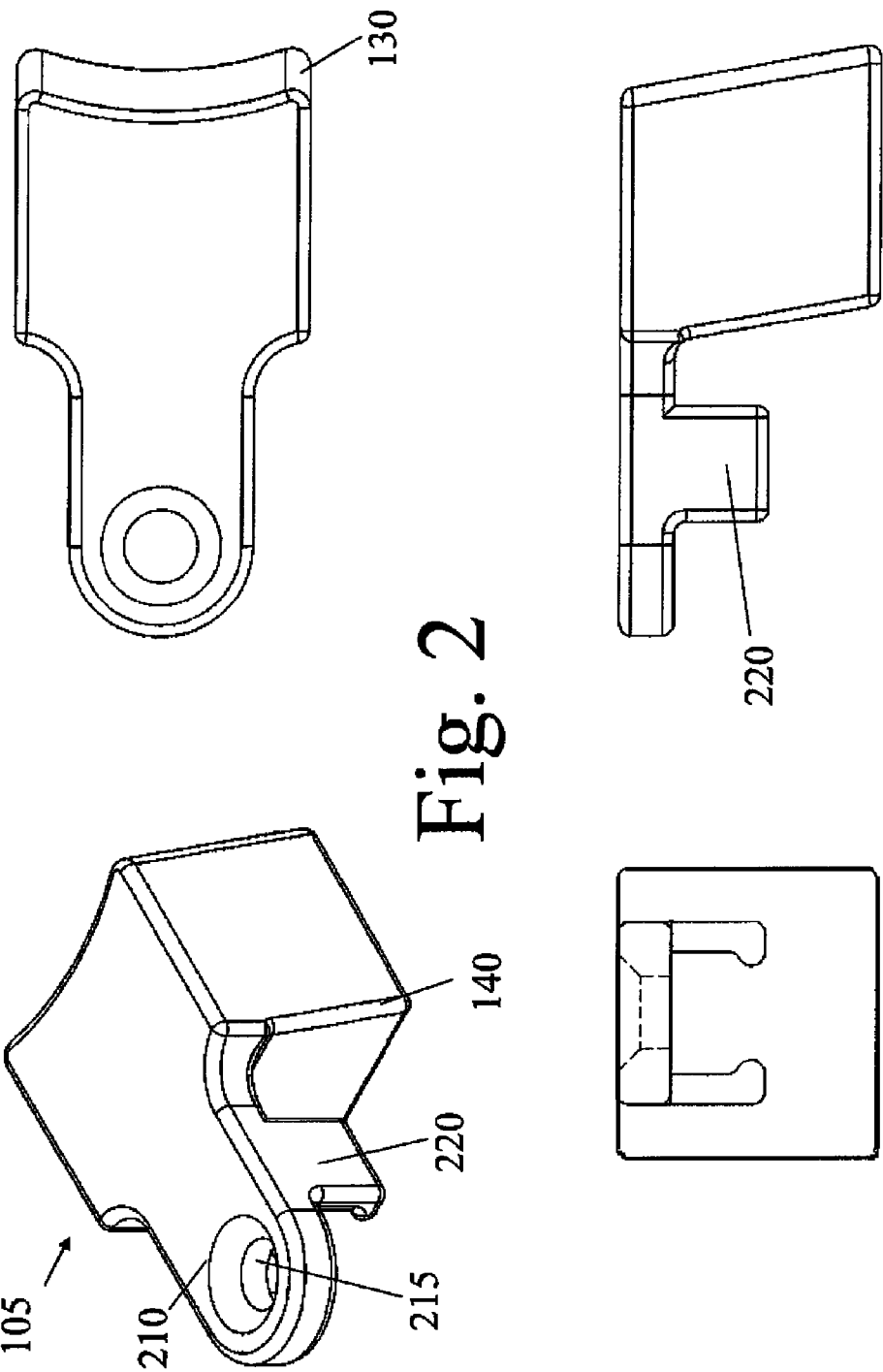

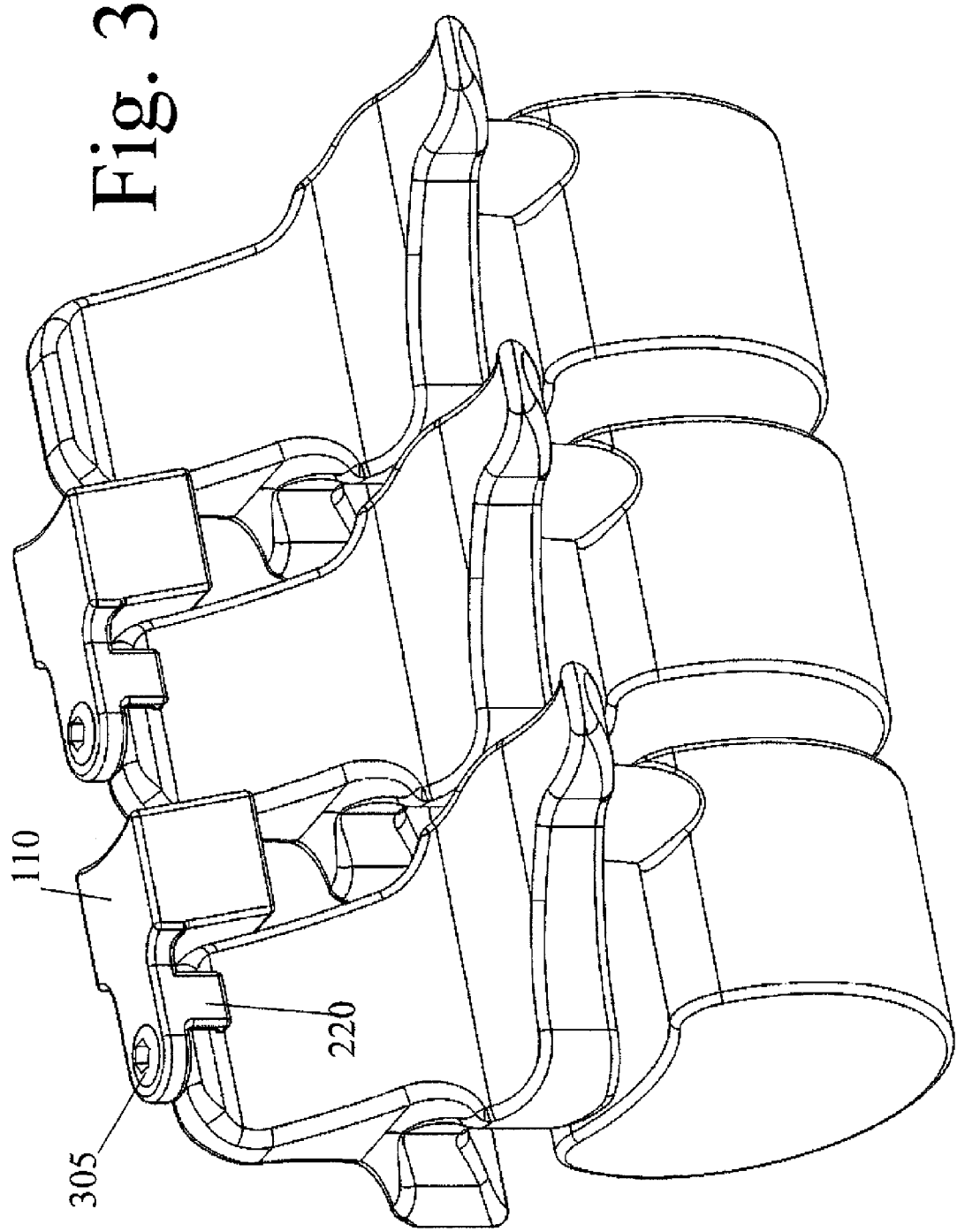

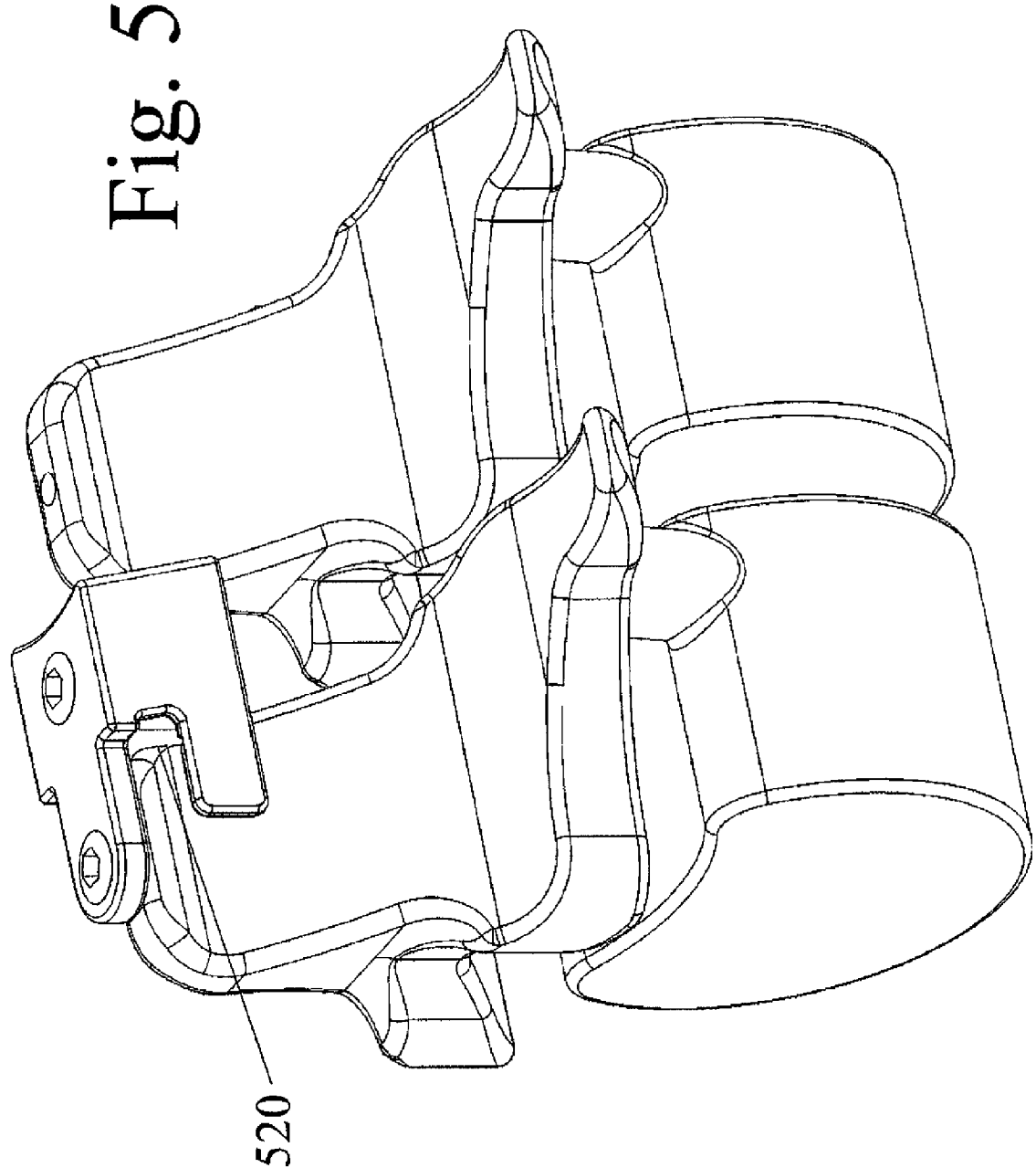

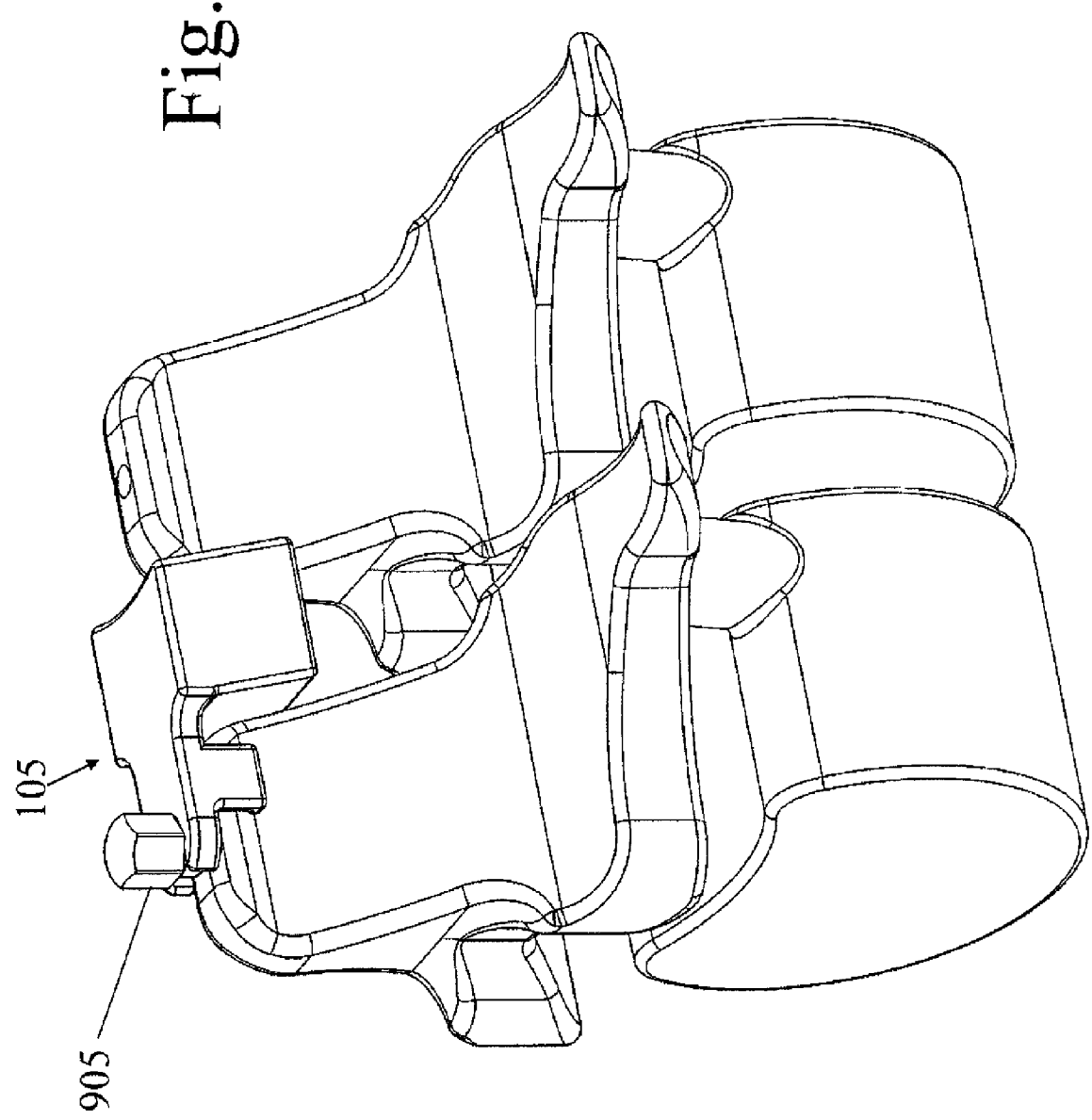

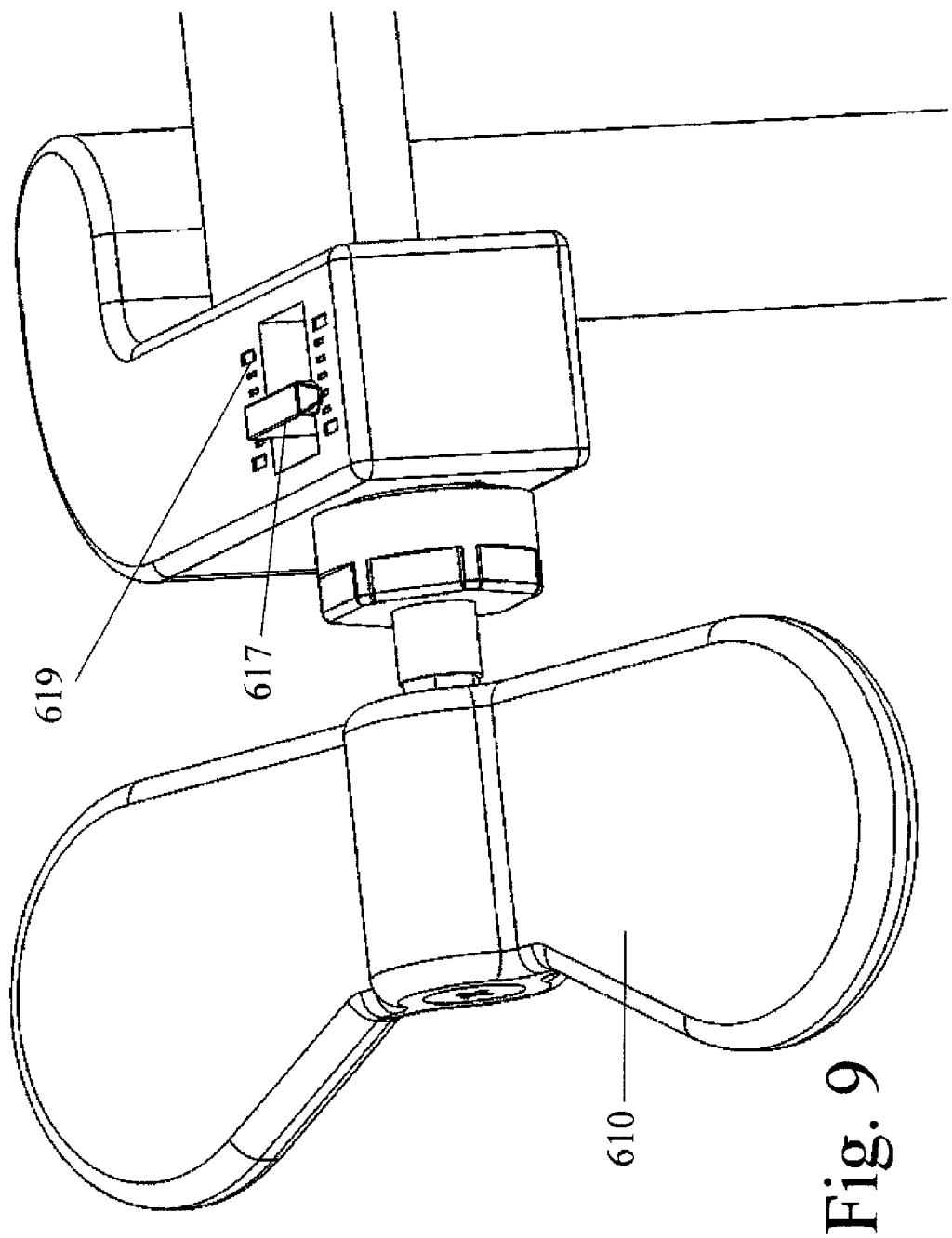

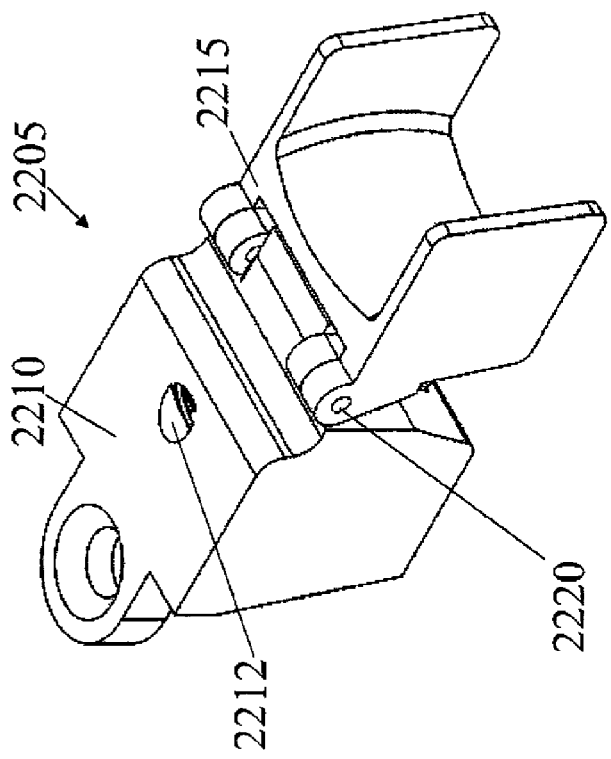
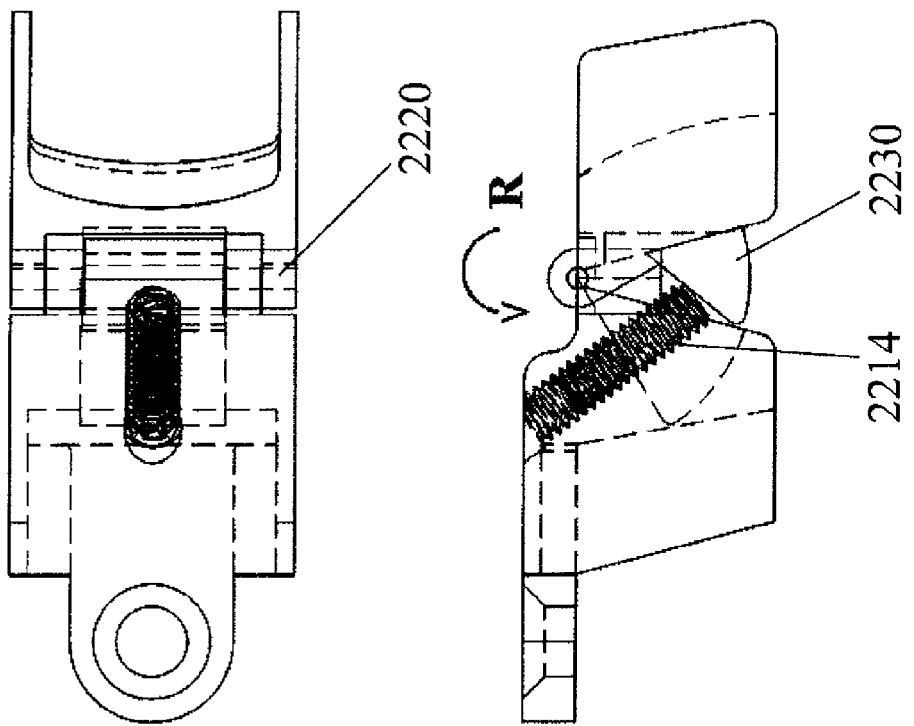

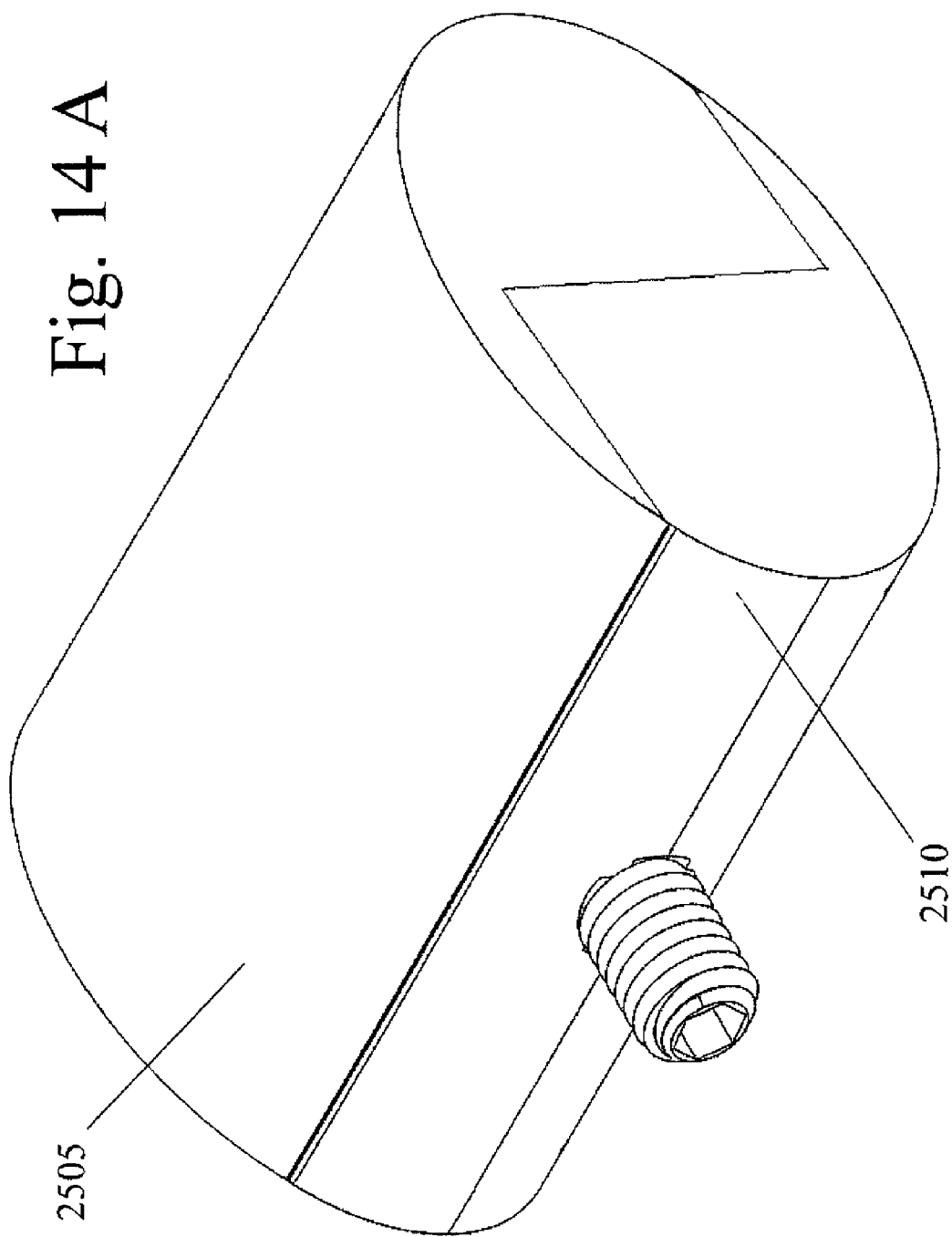

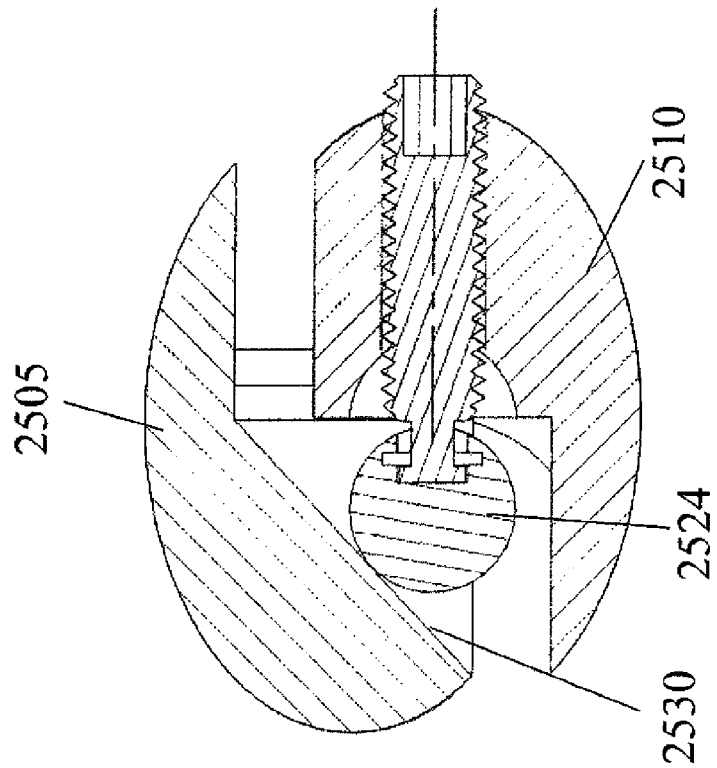
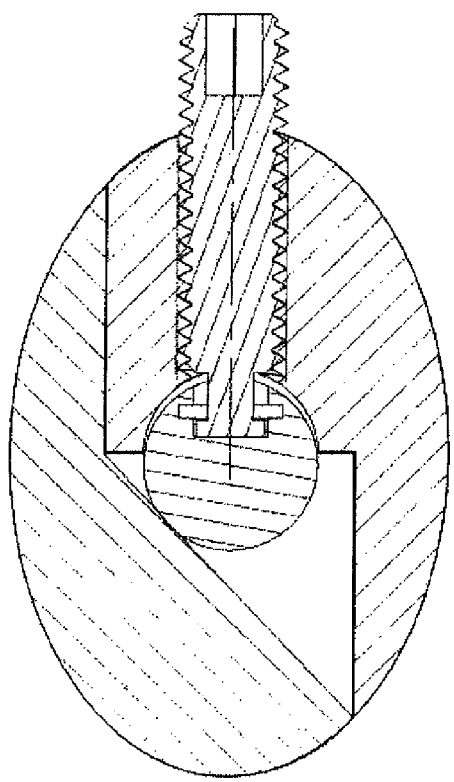
Fig. 16A
Fig. 16B

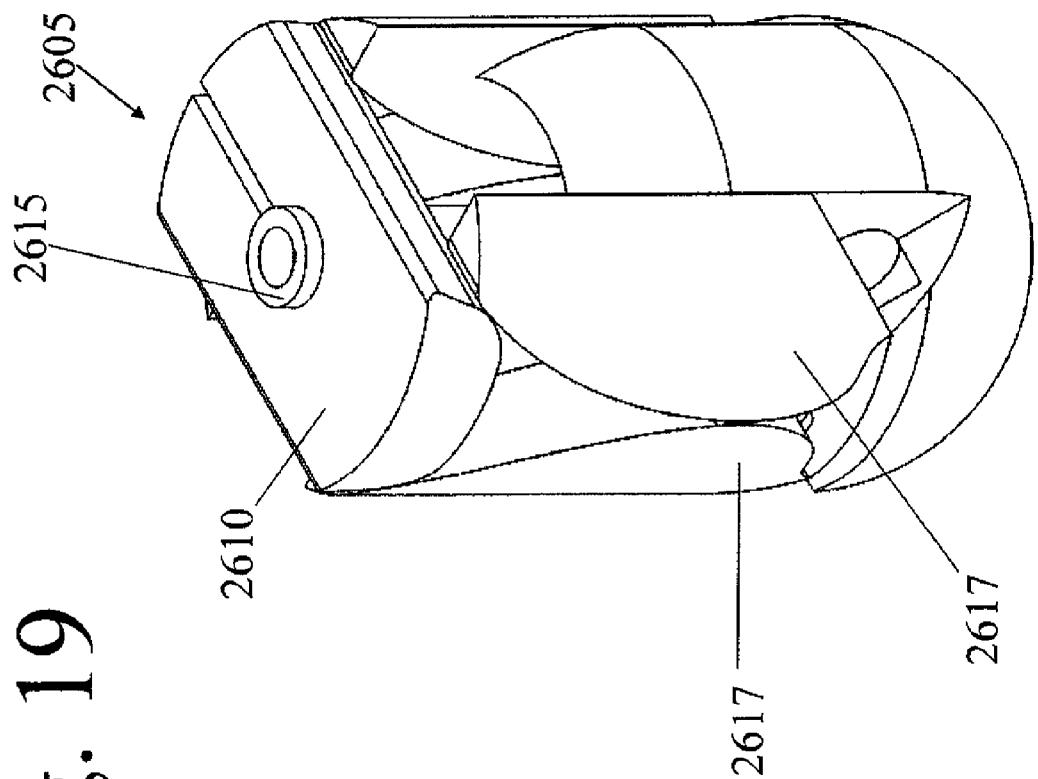
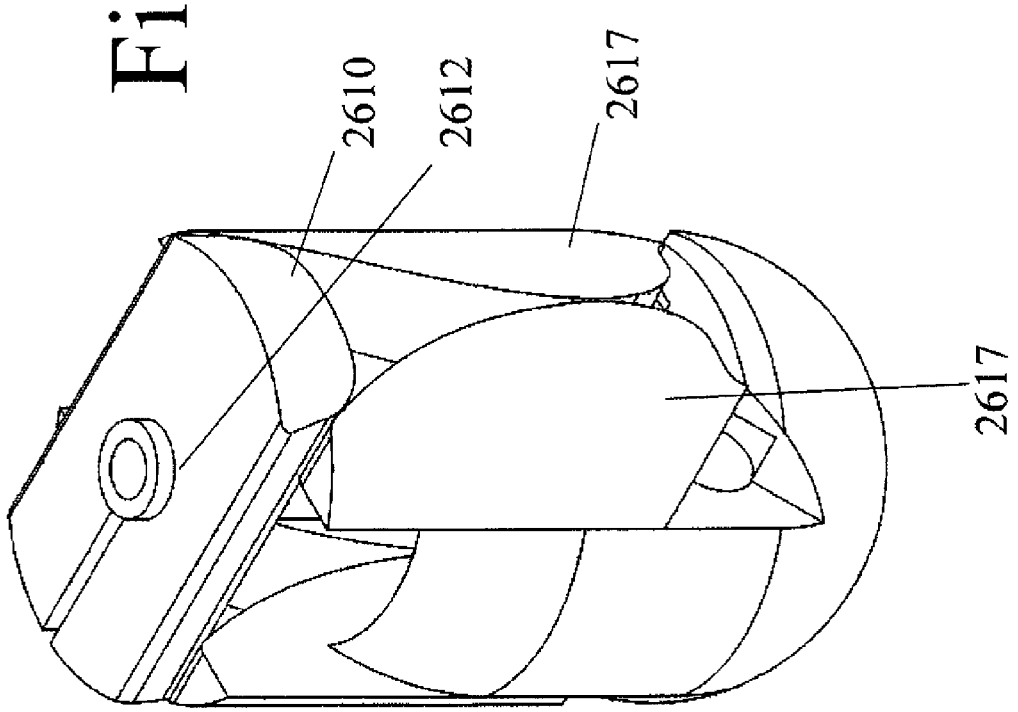
Fig. 19

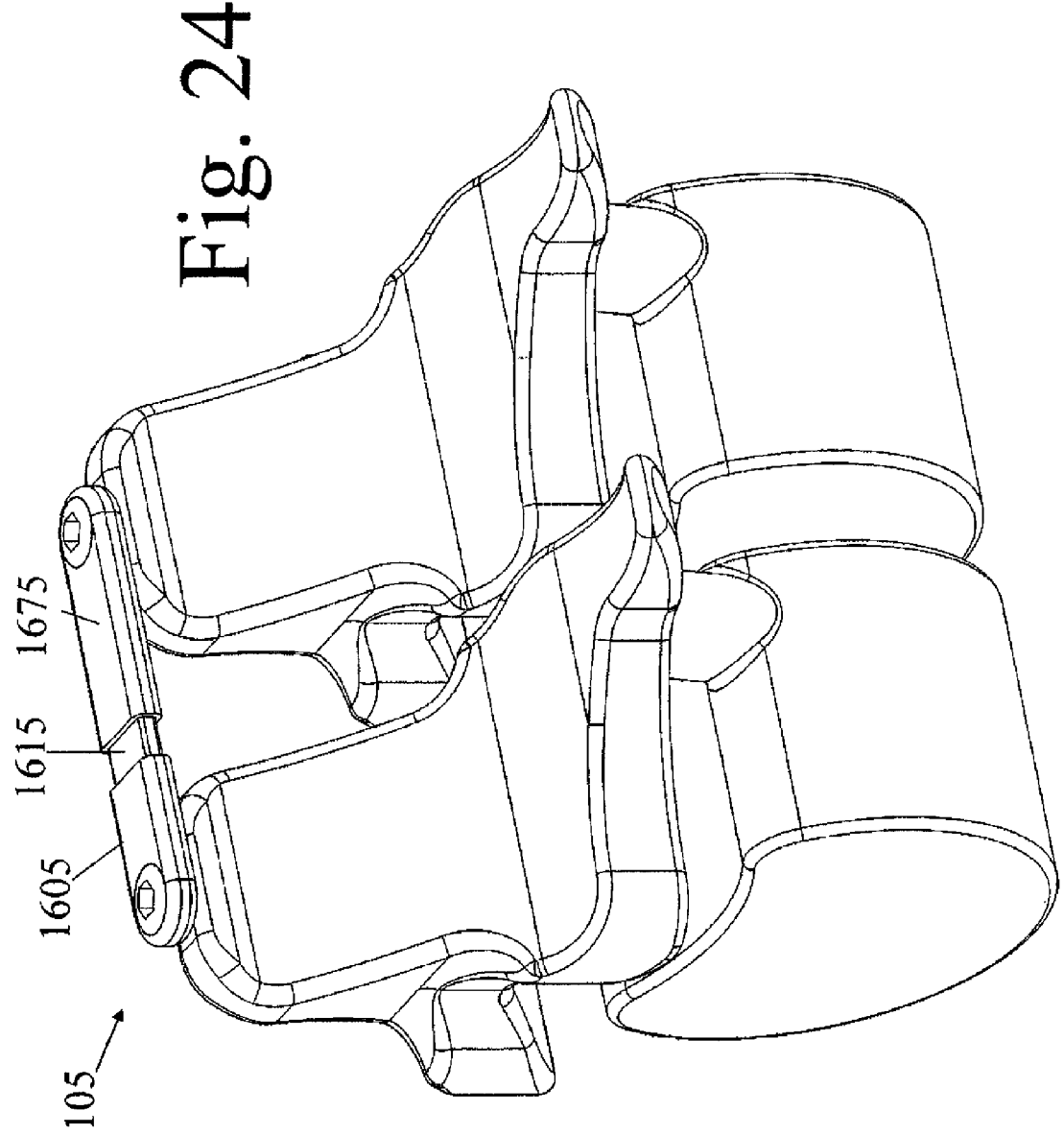

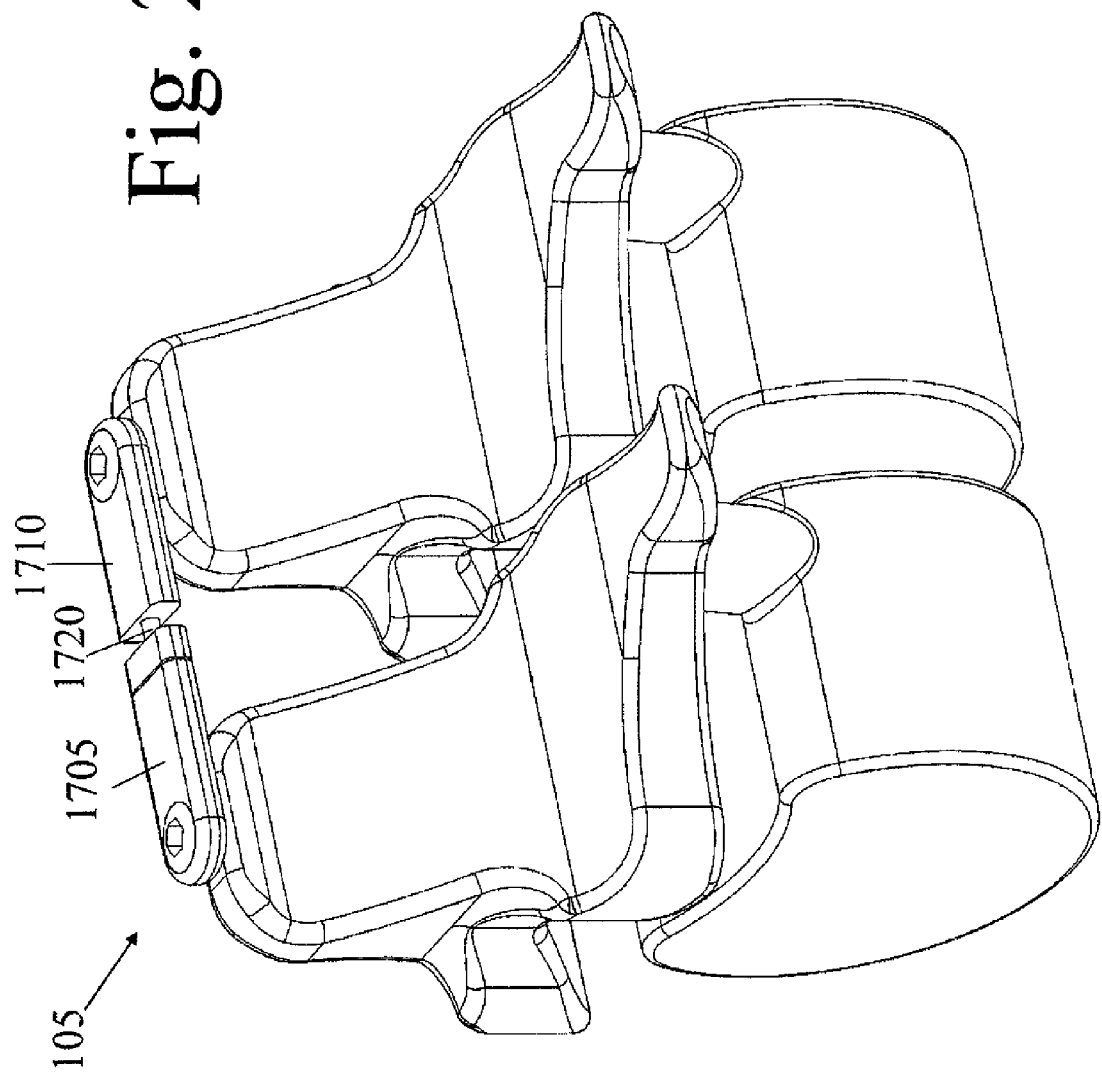

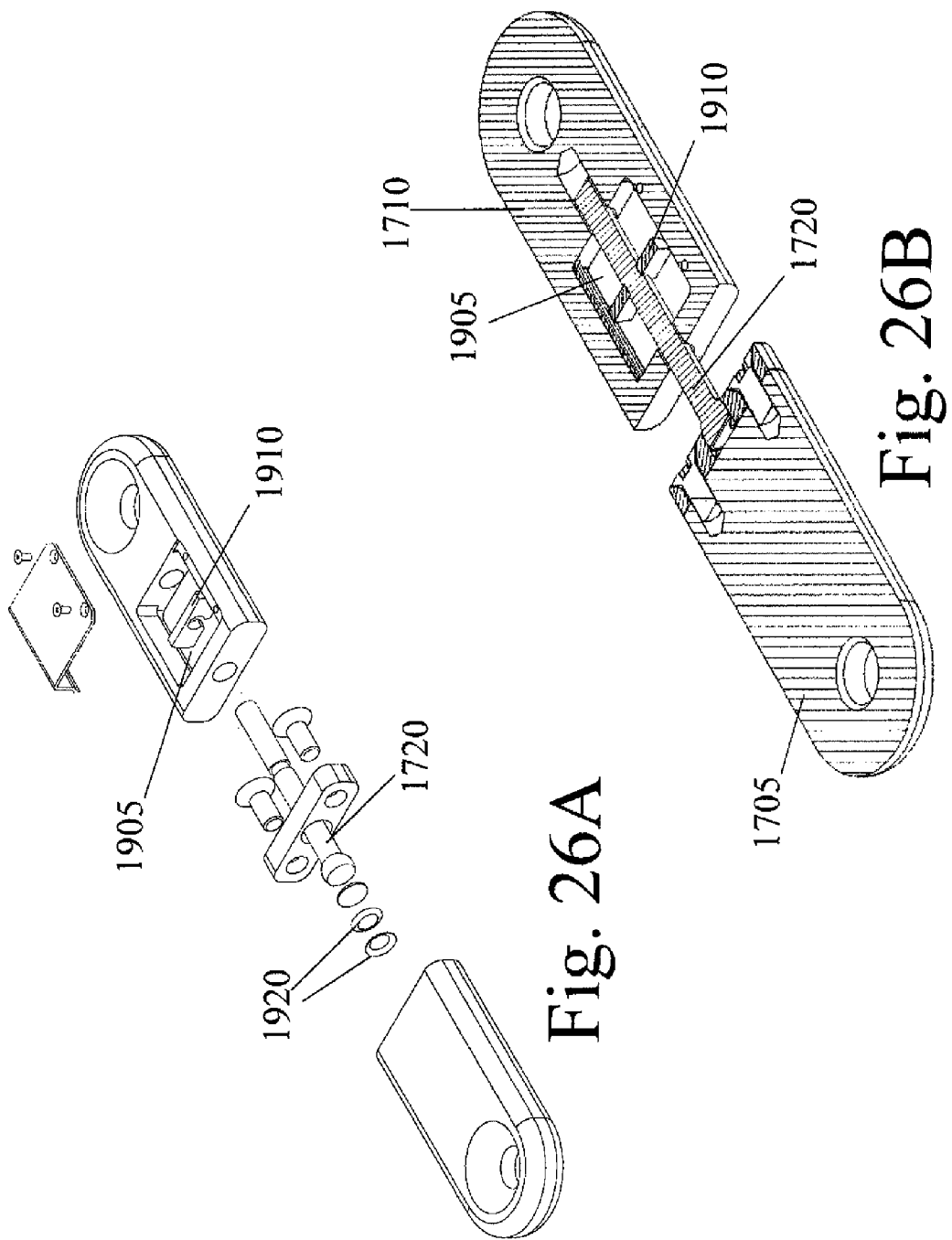

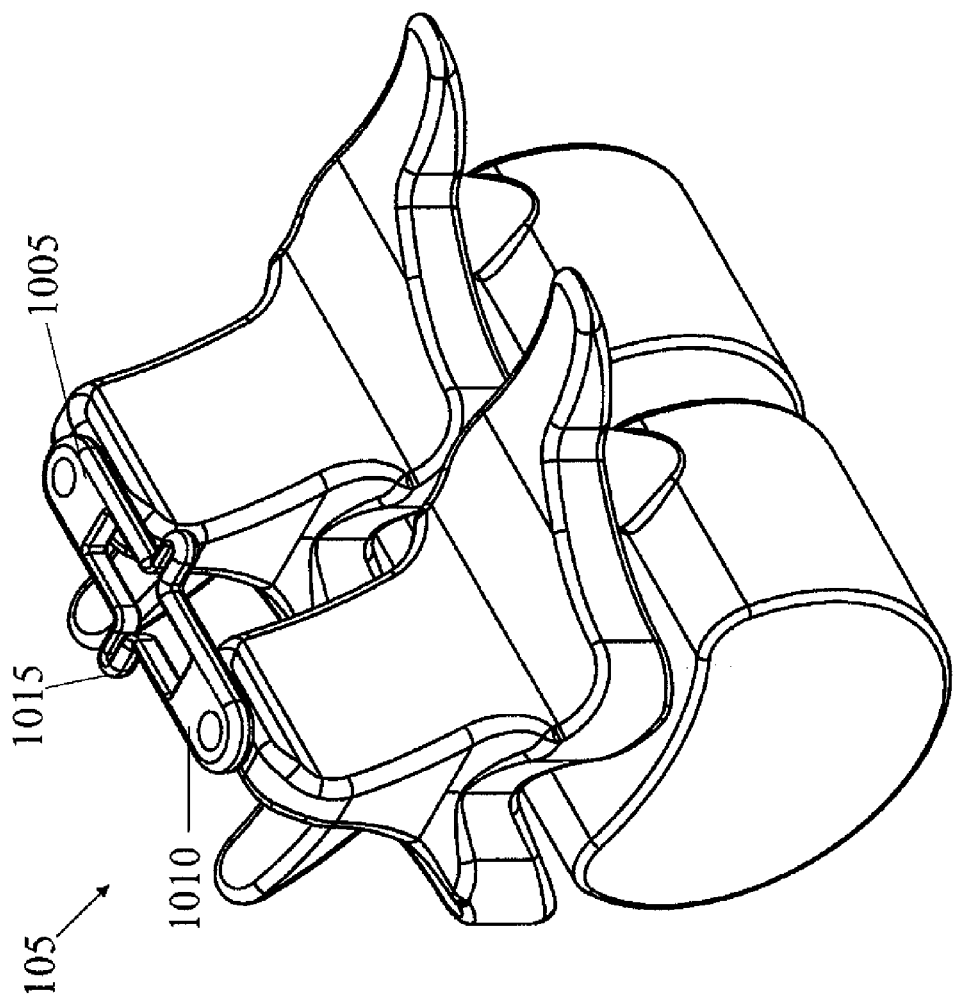

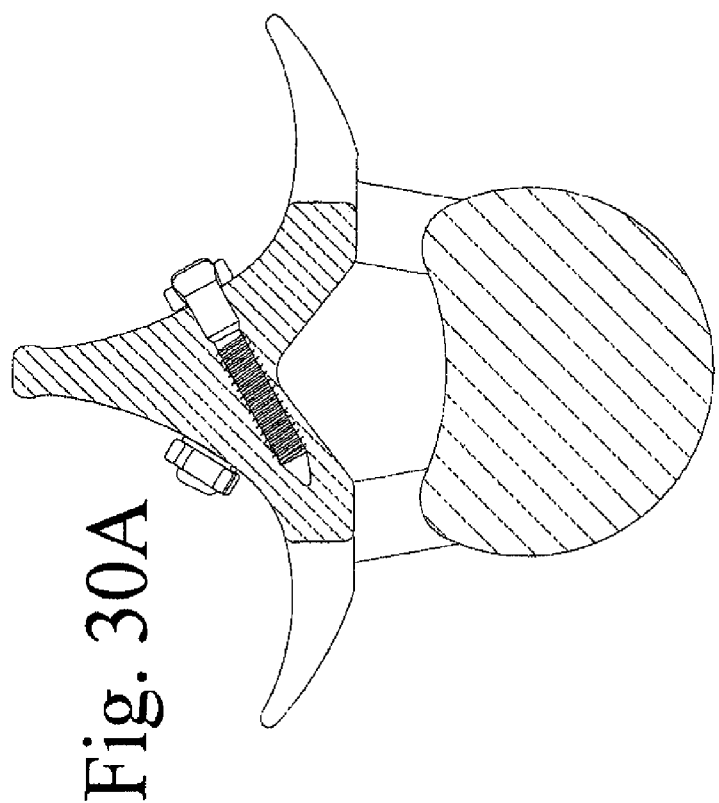
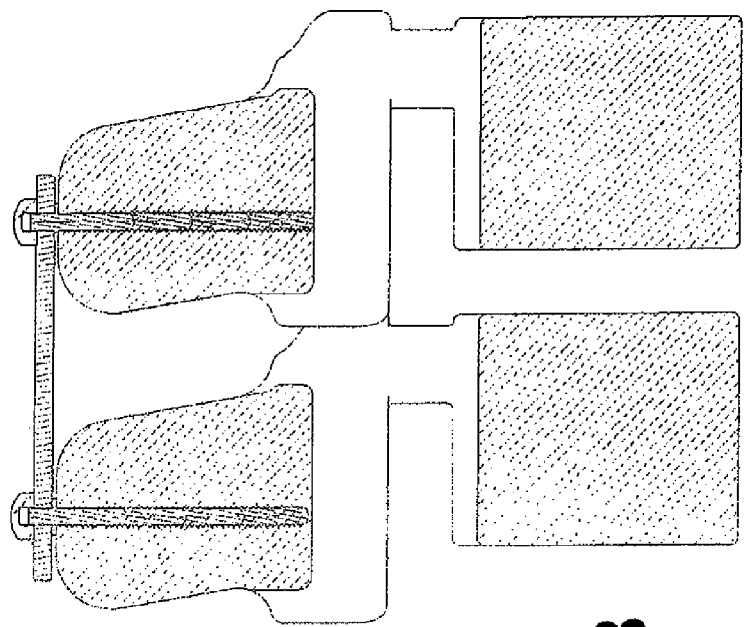
Fig. 30A
Fig. 30B

DEVICES AND METHODS FOR INTER-VERTEBRAL ORTHOPEDIC DEVICE PLACEMENT

REFERENCE TO PRIORITY DOCUMENT

This application is a continuation of U.S. patent application Ser. No. 11/613,146, filed Dec. 19, 2006, now U.S. Pat. No. 8,002,802 entitled "Devices and Methods for Inter-vertebral Orthopedic Device Placement," which claims the benefit of priority of the following U.S. Provisional Patent Applications: (1) U.S. Provisional Patent Application Ser. No. 60/751,509, filed Dec. 19, 2005; (2) U.S. Provisional Patent Application Ser. No. 60/763,411, filed Jan. 30, 2006; (3) U.S. Provisional Patent Application Ser. No. 60/792,378, filed Apr. 14, 2006; (4) U.S. Provisional Patent Application Ser. No. 60/815,296, filed Jun. 20, 2006; (5) U.S. Provisional Patent Application Ser. No. 60/815,956, filed Jun. 24, 2006; and (6) U.S. Provisional Patent Application Ser. No. 60/834,209, filed Jul. 27, 2006. Priority of the aforementioned filing dates is hereby claimed and the disclosures of the Applications are hereby incorporated by reference in their entirety.

BACKGROUND

The present disclosure is related to orthopedic devices implanted between skeletal segments. The implanted devices are used to adjust and maintain the spatial relationship(s) of adjacent bones. Depending on the implant design, the motion between the skeletal segments may be returned to normal, increased, modified, limited or completely immobilized.

Progressive constriction of the central canal within the spinal column is a predictable consequence of aging. As the spinal canal narrows, the nerve elements that reside within it become progressively more crowded. Eventually, the canal dimensions become sufficiently small so as to significantly compress the nerve elements and produce pain, weakness, sensory changes, clumsiness and other manifestation of nervous system dysfunction.

Constriction of the canal within the lumbar spine is termed lumbar stenosis. This condition is very common in the elderly and causes a significant proportion of the low back pain, lower extremity pain, lower extremity weakness, limitation of mobility and the high disability rates that afflict this age group.

The traditional treatment for this condition has been laminectomy, which is the surgical removal of the bone and ligamentous structures that constrict the spinal canal. Despite advances in surgical technique, spinal decompression surgery can be an extensive operation with risks of complication from the actual surgical procedure and the general anesthetic that is required to perform it. Since many of these elderly patients are in frail health, the risk of developing significant peri-operative medical problems remains high. In addition, the surgical resection of spinal structures may relieve the neural compression but lead to spinal instability in a substantial minority of patients. That is, removal of the spinal elements that compress the nerves may weaken the vertebral column and lead to spinal instability and vertebral mal-alignment. With instability, the vertebrae will move in an abnormal fashion relative to one another and produce pain, nerve re-impingement, weakness and disability. Further, re-stabilization of the spinal column requires additional and even more extensive surgery. Because of these issues, elderly patients with lumbar stenosis must often choose between living the remaining years in significant pain or enduring the potential life-threatening complications of open spinal decompression surgery.

Recently, lumbar stenosis has been treated by the distraction—instead of resection—of those tissues that compress the spinal canal. In this approach, an implantable device is placed between the spinous processes of the vertebral bodies at the stenotic level in order to limit the extent of bone contact during spinal extension. Since encroachment upon the nerve elements occurs most commonly and severely in extension, this treatment strategy produces an effective increase in the size of the spinal canal by limiting the amount of spinal extension. In effect, the distraction of the spinous processes changes the local bony anatomy and decompresses the nerves at the distracted level by placing the spinal segment into slight flexion.

A number of devices that utilize this strategy have been disclosed. U.S. Pat. Nos. 6,451,020; 6,695,842; 5,609,634; 5,645,599; 6,451,019; 6,761,720; 6,332,882; 6,419,676; 6,514,256; 6,699,246 and other illustrate various spinous process distractors. Unfortunately, the placement of all devices requires surgical exposure of the posterior and lateral aspects of the spinous processes as well as the posterior aspect of the spinal column. Thus, these operations still carry a significant risk of peri-operative complications in this frail patient population.

SUMMARY

This application discloses a series of novel inter-spinous implants and methods of minimally invasive placement. Bone fasteners are placed into each of the two spinous processes at the level of implantation. A distractor is used to separate the spinous processes and the implant is placed between the distracted processes. In order to standardize the procedure across patients and between different surgeons, the distractor includes an indicator that can measure the applied force of distraction. After distraction, a limited decompression of the nerve elements may be preformed, if desired, by removal of a small segment of the inferior aspect of the superior lamina and of the inferior facet surface of the superior vertebra as well as a small segment of the superior aspect of the inferior lamina and of the superior facet surface of the inferior vertebra.

After distraction and possible limited nerve decompression, an implant is placed between the adjacent spinous processes and used to maintain them in the distracted position. The implant is anchored to one or more spinous processes by bone screws or similar fasteners and functions to limit the extent of vertebral extension at the implanted level. After the implant is positioned, the distractor and distraction screws are removed. In one embodiment, a distraction screw disassembles into component members and one component serves as the fastener that attaches the implant onto bone. Multiple embodiments of the implant are illustrated.

Devices that engage and anchor into the spinous process of each of two adjacent vertebrae are also illustrated. In addition to limiting vertebral extension, these devices will control the total extent of relative vertebral motion in one or more planes at the implanted level. Several embodiments of these interspinous devices are disclosed. Combination implants are also illustrated.

In one aspect, there is disclosed a spinal implant device, comprising: a spacer region adapted to be positioned between first and second spinous processes of first and second vertebral bodies to limit movement of the first spinous process and the second spinous process toward one another; and an attachment region attached to the spacer region, the attachment region adapted to attach to the first spinous process via a fastener that extends substantially along a long axis of the spinous process.

In another aspect, there is disclosed a spinal implant device, comprising: a first attachment region that attaches to a first spinous process via a fastener that extends substantially along a long axis of the first spinous process; and a second attachment region that attaches to a second spinous process, wherein the first attachment region and the second attachment region can move a limited distance toward one another and a limited distance away from one another to limit relative movement between the first and second spinous processes.

In another aspect, there is disclosed a spinal implant device, comprising: a plate having a first attachment region that attaches to a first spinous process and a second attachment region that attaches to a second spinous process, the plate further having a spacer region between the first and second attachment regions, the spacer region adapted to permit relative movement between the first and second attachment regions.

In another aspect, there is disclosed a method of stabilizing the spine, comprising: attaching a first portion of a spinal implant to a first spinous process of a first vertebral body wherein the first portion of the spinal implant is attached to the long axis of the first spinous process; and attaching a second portion of the spinal implant to a second spinous process of a second vertebral body, wherein the spinal implant limits movement of the first spinous process relative to the second spinous process.

In another aspect, there is disclosed a method of stabilizing the spine, comprising: fastening a first distraction member to a first spinous process of a first vertebral body wherein the distraction screw extends along a long axis of the first spinous process; attaching a second distraction member to a second spinous process of a second vertebral body; distracting the first and second spinous processes using the first and second distraction members; and placing an implant between the first and second spinous processes wherein the implant modulates relative movement between the first and second spinous processes.

In another aspect, there is disclosed method of stabilizing the spine, comprising: removing a segment of the inferior aspect of the superior lamina and a segment of the inferior facet surface of the superior vertebra; removing a segment of the superior aspect of the inferior lamina and a segment the superior facet surface of the inferior vertebra; and placing an implant between the superior lamina and the superior vertebra.

In another aspect, there is disclosed a spinal implant device for controlling vertebral motion, comprising an attachment region adapted to attach to a first spinous process via a fastener that extends substantially along a long axis of the spinous process.

In another aspect, there is disclosed a spinal implant device for controlling vertebral motion, comprising an attachment region adapted to attach to a first spinous process via a fastener that extends substantially along a long axis of the lamina.

In another aspect, there is disclosed a spinal implant device for controlling vertebral motion, comprising an attachment region adapted to attach to a first spinous process via a fastener that extends toward a midline of the lamina.

In another aspect, there is disclosed a spinal implant device for controlling vertebral motion, comprising an attachment region adapted to attach to a first spinous process via a fastener that extends toward a superior aspect of the midline of the lamina.

In another aspect, there is disclosed a spinal implant device for controlling vertebral motion, comprising an attachment region adapted to attach to a first spinous process by clamping onto sides of the lamina on both sides of the vertebral midline.

In another aspect, there is disclosed a spinal implant device for controlling vertebral motion, comprising a first segment that attaches to a first vertebral body; a second segment that attaches to a second vertebral body, the first and second segments being movable relative to one another to vary the length of the spinal implant; and a spacer region that positions between first and second spinous processes of the first and second vertebral bodies.

In another aspect, there is disclosed a spinal implant device for controlling vertebral motion, comprising a spring formed of a coiled, elongated member, the spring extending along an axis and adapted to be positioned between a pair of spinous processes, wherein a first end of the elongate member attaches to a first spinous process and a second end attaches to a second spinous process.

The implants described provide dynamic spinal stabilization while permitting minimally invasive placement. Other features and advantages will be apparent from the following description of various embodiments, which illustrate, by way of example, the principles of the disclosed devices and methods.

BRIEF DESCRIPTION OF THE DRAWINGS

FIG. 1 shows a perspective view of a device that is configured for placement between the spinous processes of two adjacent vertebral bodies.

FIG. 2 shows perspective, top, front, and side views of the device of FIG. 1.

FIG. 3 shows a pair of devices at adjacent vertebral segments.

FIG. 5 shows the device of FIGS. 4A-4D attached onto the spinous process between vertebral bodies.

FIG. 8 shows a lock nut locking the device to a vertebral body.

FIG. 9 shows an enlarged view of a portion of the distractor device.

FIGS. 12A, 12B, and 13 illustrate an additional embodiment wherein the implant can expand and vary in size.

FIGS. 14A to 18B illustrate two additional mechanisms that will produce expandable implants.

FIGS. 19-21 show another embodiment of an expandable implant.

FIG. 24 shows another embodiment of the interspinous device that permits relative movement between the vertebral bodies.

FIG. 25 shows another embodiment of an interspinous device that includes first and second attachment regions that are movably attached to one another.

FIGS. 26A and 26B show exploded and cross-sectional views of the device of FIG. 25.

FIG. 27 shows yet another embodiment of an interspinous device.

FIGS. 30A, 30B, 31A, and 31B show cross-sectional views of interspinous devices attached to bone.

DETAILED DESCRIPTION

Figure 4A:
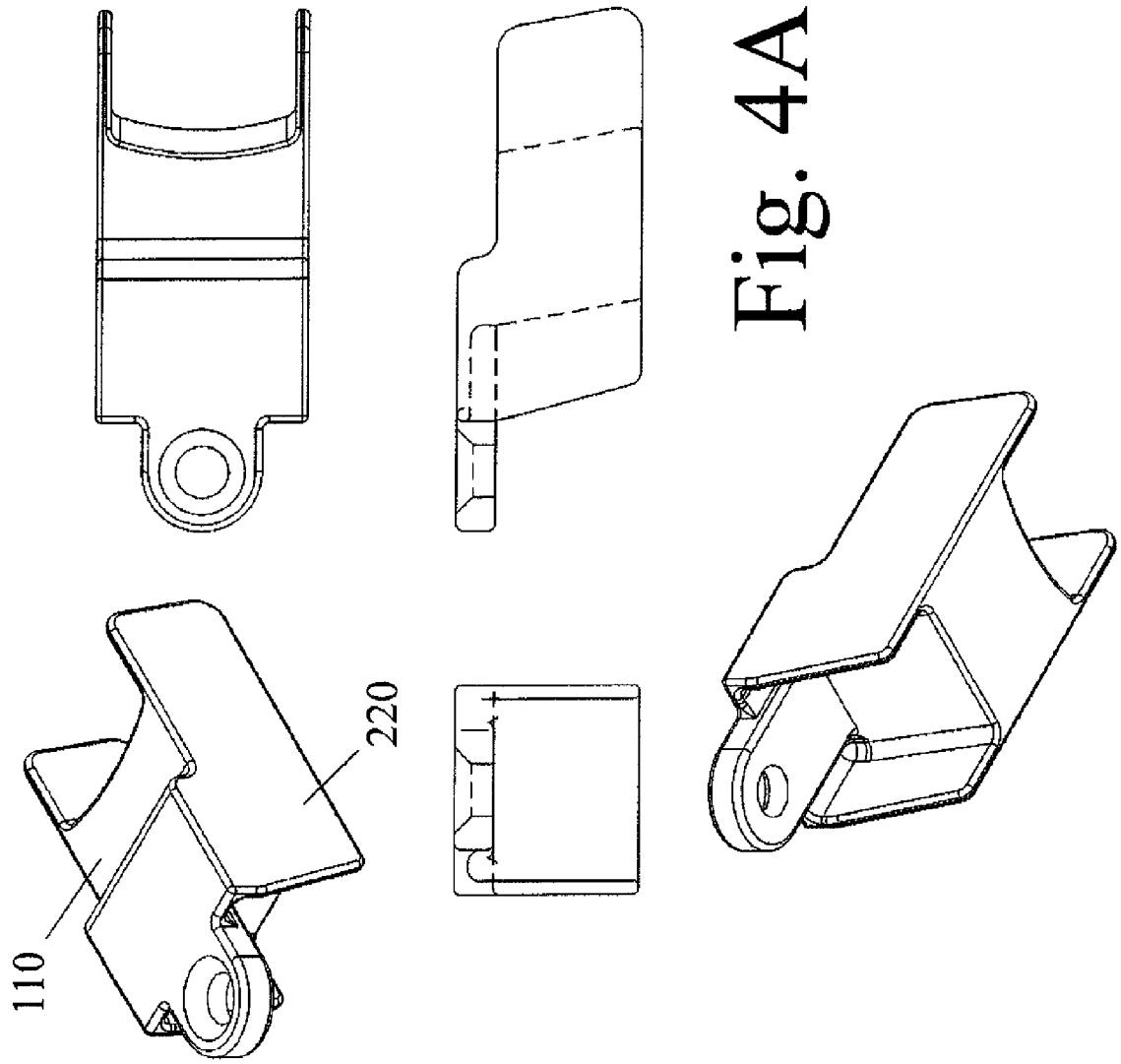
FIGS. 4A-4D show another embodiment of the device wherein the device includes a cavity for receipt of a bone graft or segment.

FIG. 1 shows a perspective view of a device 105 that is configured for placement between the spinous processes of two adjacent vertebral bodies. The device 105 includes a spacer region or central region 110 that is sized and shaped to fit between the spinous processes of the two adjacent vertebral bodies. The device 105 further includes at least one attachment region 115 that is adapted to attach and anchor onto the spinous process of at least one of the vertebral bodies. The central region 110 can have a variety of shapes and sizes for placement between the spinous processes. The attachment region 115 can also have various sizes and shapes for attachment to the spinous processes. For clarity of illustration, the vertebral bodies are represented schematically and those skilled in the art will appreciate that actual vertebral bodies include anatomical details not shown in FIG. 1.

FIG. 2 shows perspective, top, front, and side views of the device 105 of FIG. 1. The central region 110 is sized and shaped to fit between the spinous processes of the two adjacent vertebral bodies. In this regard, the central region 110 is shown as a rectangular body, although the central region 110 can be spherical, elliptical, oval, or any other shape that fits between the spinous processes. The device preferably has a distal protrusion 130 that at least partially extends onto either side of the adjacent spinous process. The attachment region 115 includes an upper wall 210 having a borehole 215 for receipt of a fastener such as a bone screw. The inferior surface of the attachment region 115 may be further grooved or otherwise textured to provide increased bone contact and resistance to rotation. One or more anchor protrusions, such as flaps 220, extend downwardly from the upper wall 210 or may extend backwards to at least partially extends onto either side of the spinous process to which the device is attached. While shown attached to the inferior spinous process, the device may be alternatively attached to the spinous process above the implanted inter-spinous space (that is, the superior spinous process).

FIG. 3 shows a pair of devices 105 at adjacent vertebral segments. Each device 105 is implanted relative to the vertebral bodies such that two side flaps 220 straddle the spinous process and aid in attaching the device 105 onto the spinous process. The central region 110 is positioned between the spinous processes. In an alternate embodiment, the flaps 220 can be attached onto the central region 110 to straddle a different surface of the spinous process. One or more attachment screw(s) 305 can be inserted through the borehole for anchoring the device 105. The attachment screw(s) may be alternatively (or additionally) used to anchor onto the side of the spinous process through one flap or serve to connect both side flaps so as to completely cross the spinous process from side to side.

An alternative embodiment is shown in FIG. 4A with a different flap arrangement. The side flaps are configured to at least partially extend onto either side of each of the spinous processes. Many different flap arraignments can be configured and devices with various flap arraignments are considered to fall within the general scope of the invention. Moreover, any surface of the disclosed implants that contacts bony may be further textured to increase frictional bone contact and/or coated or treated using one of the many known techniques that increase bony ingrowth and osseous integration at the implant-bone interface (such as porous coating, addition of hydroxyapatite coating, incorporation of bone or growth factors and the like).

Figure 4C:
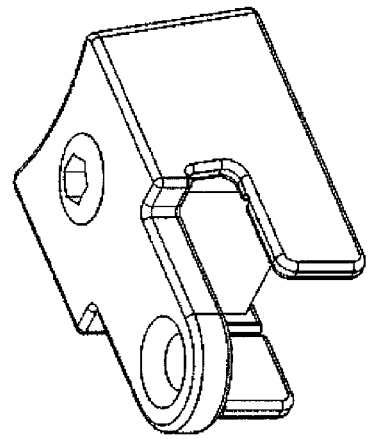
Figure 4D:
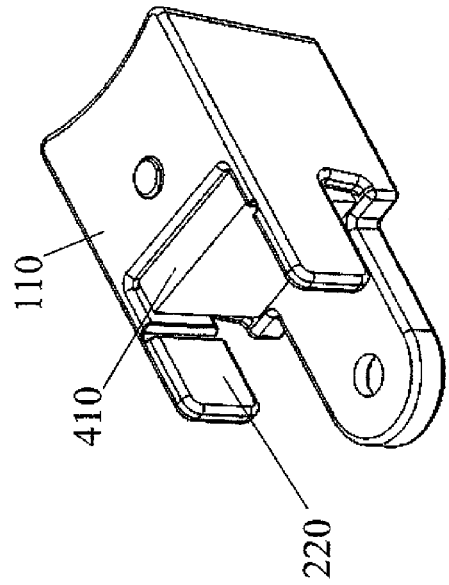
Figure 4B:
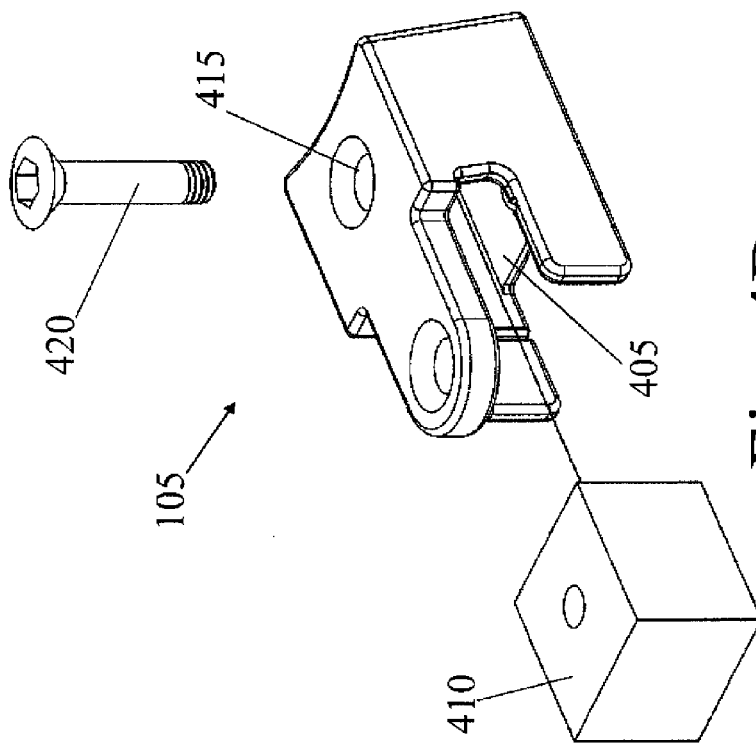

FIGS. 4B, 4C, and 4D show another embodiment of the device 105 wherein the device 105 includes a cavity 405 for receipt of a bone graft or segment 410. In the embodiment of FIGS. 4B-4D, the device 105 includes flaps 220 that extend outward from the central region 110 rather than extending from the attachment region 115 as in the previous embodiment. In addition, the device 105 includes a borehole 415 for receipt of a fixation device 420, such as a screw, that fixates the bone graft 410 to the device 105.

FIG. 5 shows the device 105 of FIGS. 4B-4D attached onto the spinous process between vertebral bodies. During implantation, the bony surface of the spinous process that comes into contact with the bone graft 410 of the device 105 is decorticated and cut so as provide a suitable surface for bone growth and fusion. Interface 520 marks the area of apposition of decorticated spinous process surface and the bone graft portion of the implant.

An exemplary method of implanting the device 105 is now described with reference to FIGS. 6-8. The method of implantations is described using a particular embodiment of the device 110 although it should be appreciated that the method of implantation can be used with any of the device embodiments. The implantation method uses distraction screws and a distractor device to standardize the extent of vertebral distraction and hasten device placement. FIG. 6A shows a pair of distraction screws 505 and 510 positioned adjacent the vertebral bodies. The distraction screws 505 and 510 include shanks that can be fixated into the spinous processes. In one embodiment, at least one screw is optionally a multi-segmental screw that can be detached into two or more segments after it is attached to the spinous process.

Figure 6B:
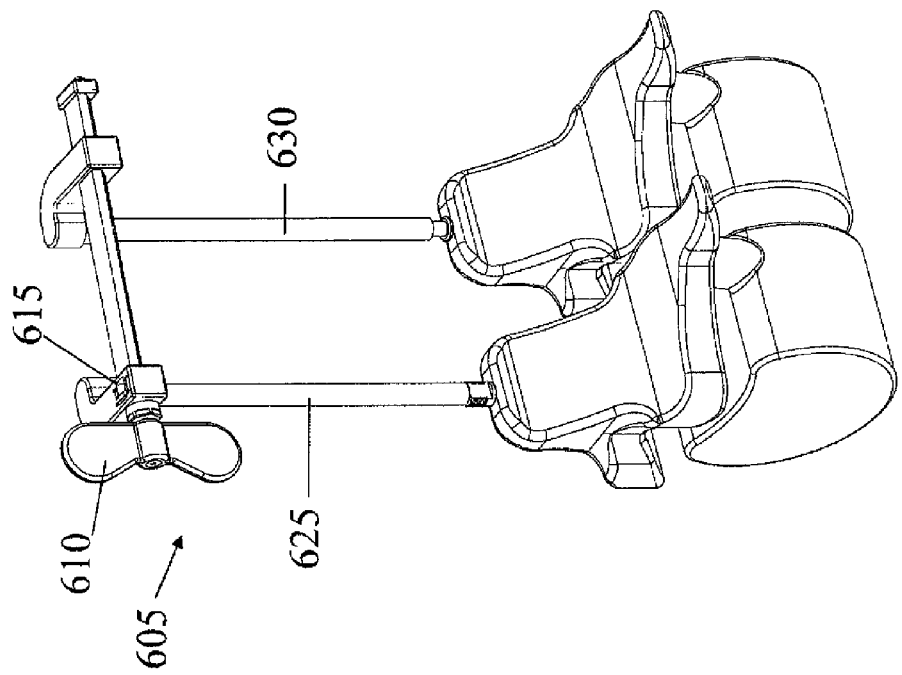
FIG. 6B shows distraction screws attached to the spinous processes of the vertebral bodies and a distractor device mounted on the distractor screws.
Figure 6A:
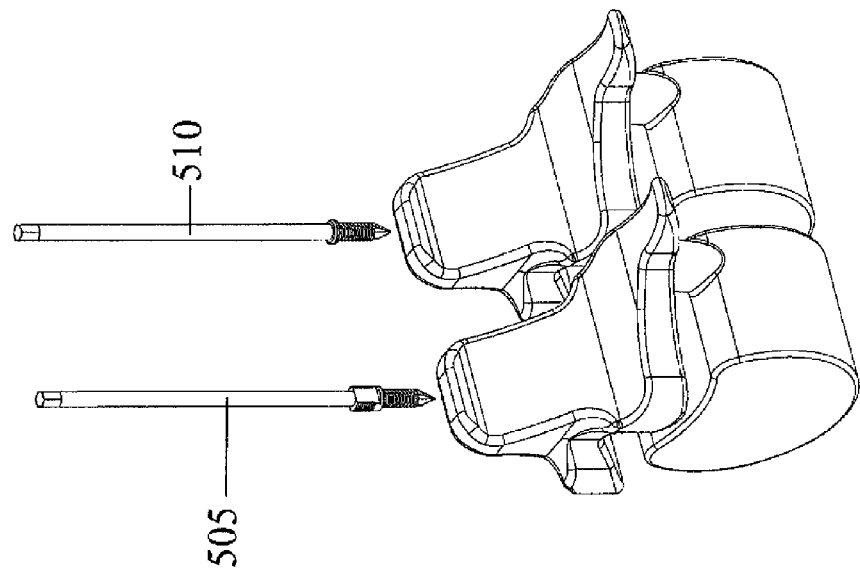
FIG. 6A shows distraction screws prior to being attached to the spinous processes of the vertebral bodies

FIG. 6B shows the distraction screws 505 and 520 attached to the spinous processes of the vertebral bodies and a distractor device 605 mounted on the distractor screws. The distraction device 605 includes a platform that can be actuated using an actuator 610 to apply a distraction force to the distraction screws 505 and 510. Upon actuation of the actuator 610, the platform exerts a distraction force to separate the distraction screws. The distraction can be maintained while the implant is placed between them, as described below. The distractor can include an indicator 615 that is capable of measuring the force of distraction providing an indication as to the amount of distraction force being applied (discussed below). In this way, the extent of distraction is standardized across patients of differing anatomy and is no longer determined by subjective "feel" on the part of the operating surgeon.

Figure 7B:
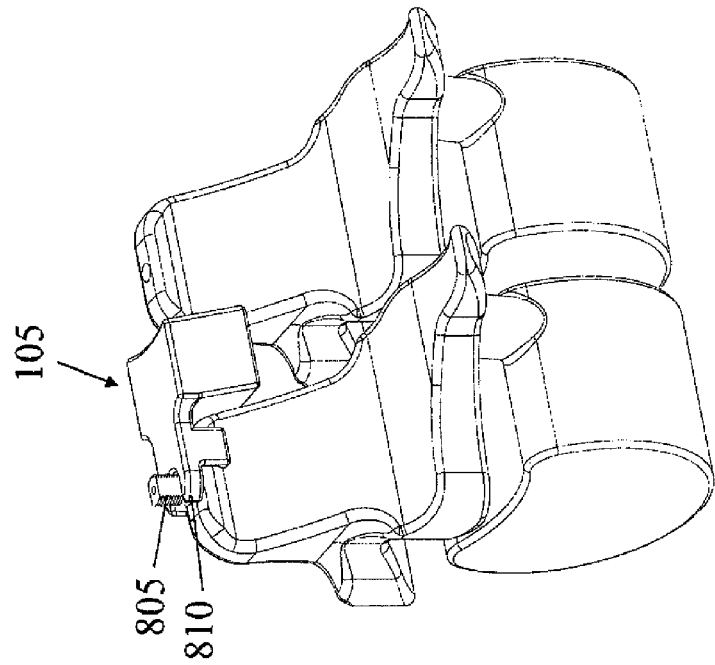
FIG. 7B shows the device positioned between the vertebral bodies with a portion of the distraction screw extending upwardly through an opening.
Figure 7A:
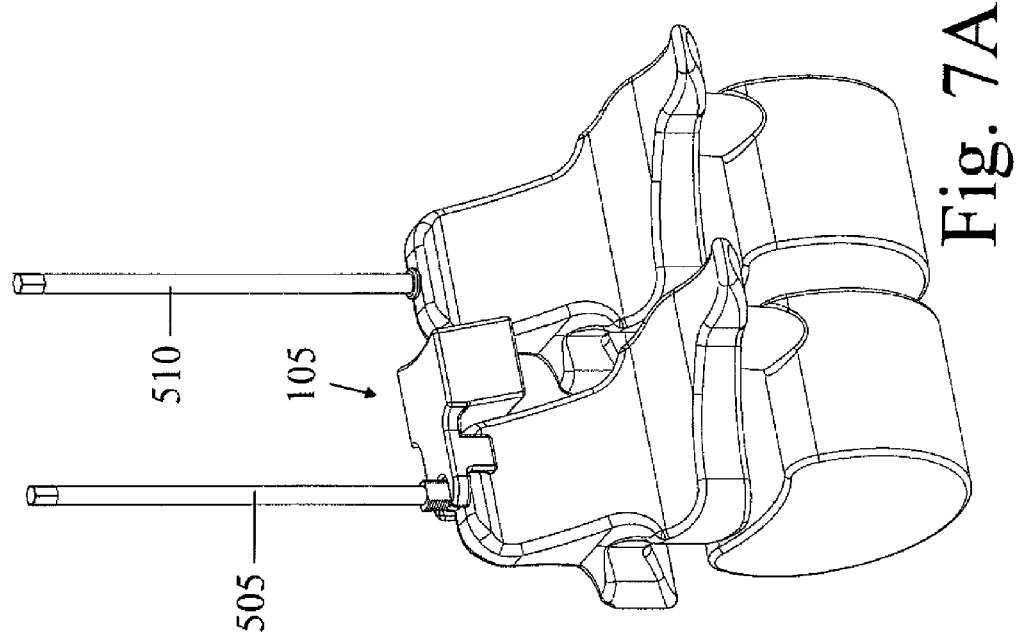
FIG. 7A shows the device positioned between the vertebral bodies with the distraction screws still attached to the vertebral bodies.

With the distraction device 605 in place and the segment appropriately distracted, the distance between the two spinous processes is measured and a device 105 of sufficient size is chosen based on the measured distance. The device 105 is lowered into position such that the central region 110 is located between the distracted spinous processes. The distraction device is then removed and the central region 110 of the device 105 maintains the spinous process in the distracted position. FIG. 7A shows the device 105 positioned between the vertebral bodies with the distraction screws 505 and 510 still attached to the vertebral bodies. The distraction screw 505 includes a proximal region that can be unattached from the shank of the distraction screw.

Next, the proximal region is removed from the shank of the distraction screw 505 and the distraction screw 510 is completely removed from the vertebral body. FIG. 7B shows the device 105 positioned between the vertebral bodies with a portion 805 of the distraction screw 505 extending upwardly through an opening 810, such as a hole or slot, in the device 505. Thus, the portion 805 and the attachment region 115 of the device 105 are both attached to the spinous process. With reference to FIG. 8, a retainer, such as a nut 905, is coupled to the portion 805 and used to lock the attachment region 115 of the device 105 onto the portion 805 and to the underlying spinous process. As mentioned, the other distraction screw is removed in its entirety. The implantation procedure provides a fast, reliable and reproducible method of interspinous implant placement.

Figure 10:
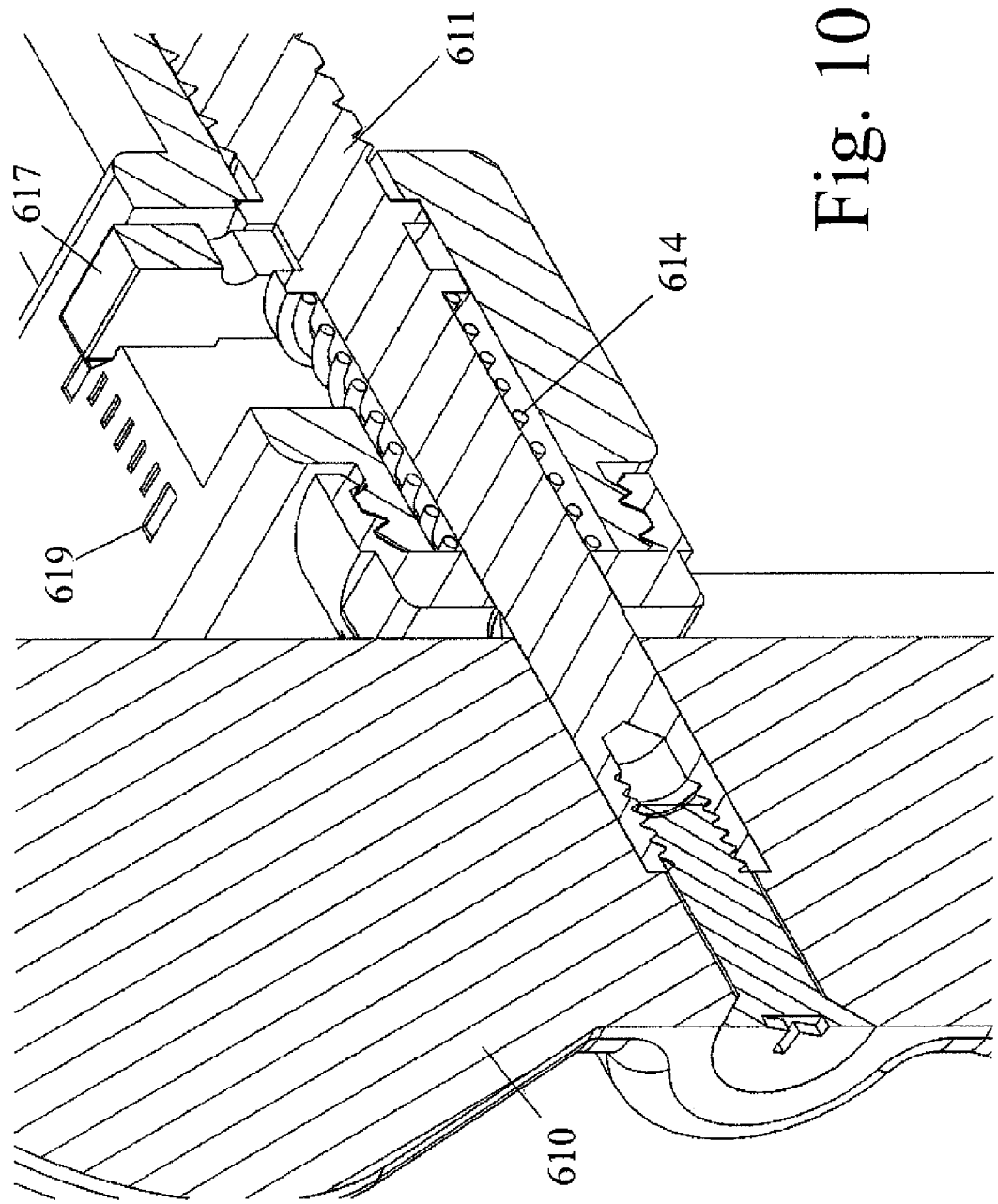
FIG. 10 shows an enlarged, cross-sectional view of a portion of the distractor device.

FIG. 9 shows a magnified view of one end of the distraction device or while FIG. 10 illustrates a sectional view through that end. The force measurement adapter is shown. With rotation of actuator 610 and the attached leadscrew 611, the two protrusions 625 and 630 (that house distraction screws 505 and 510) of the distraction platform are separated and the force of distraction is transmitted onto the contained distraction screws. As shown in FIG. 10, leadscrew 611 is surrounded by spring 614 and the leadscrew engages pointer 617. As leadscrew 611 turns and members 625 and 630 are distracted, pointer 617 will move relative to marking 619 in manner directly related to the force of distraction. The hatch markings 619 may provide an actual measure of the distraction force in a recognized physical unit or simply give an arbitrary number, letter, or designation to which the operator would distract the vertebral bodies. Using this feature, the force of distraction applied during the procedure can be standardized.

Figure 11A:
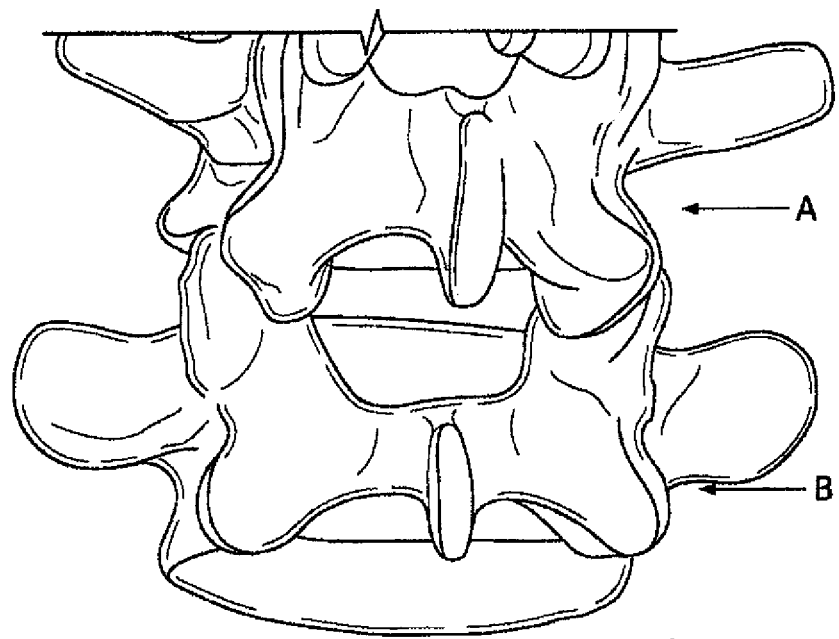
FIGS. 11A and 11B illustrate an optional step within the implantation procedure.
Figure 11B:
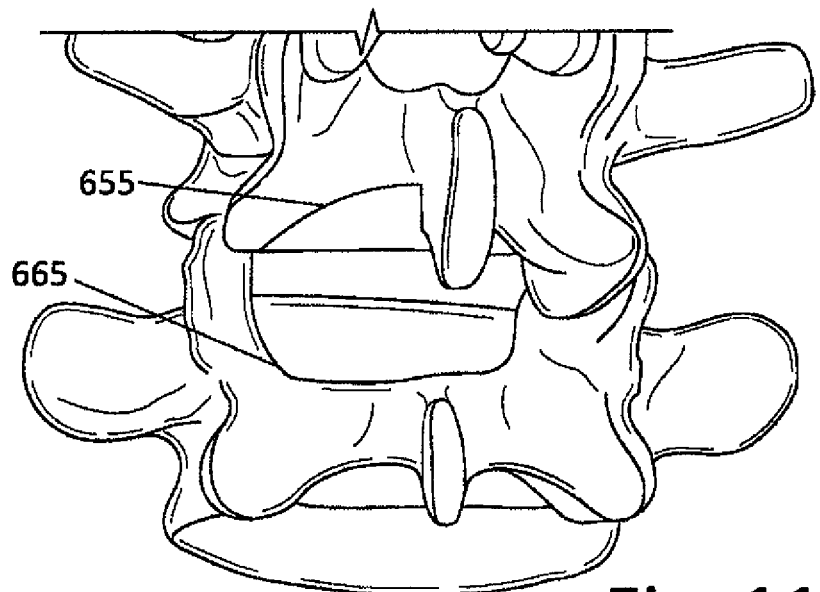

FIGS. 11A and 11B illustrate an optional step within the implantation procedure. After vertebral distraction but before device implantation, the surgeon may directly decompress the nerve elements by removing a small segment of bone and ligament. The application of distraction before boney resection better defines the anatomical landmarks and allows the surgeon to precisely define the compressive elements. Using the pre-distraction technique, the decompression is more precisely tailored to the individual patient and the extent of resection is significantly reduced. The extent of decompression illustrated is substantially less than traditional laminectomy. FIG. 11A shows a schematic representation of an intact spinal level consisting of two vertebral bodies A & B. FIG. 11B shows the resection performed on one side. For diagrammatic simplicity, the distraction screws and distraction device are not shown. However, in actual practice, the resection is performed with the devices in place. With respect to FIG. 11B, the decompression is performed by removal of a small segment of the inferior aspect of the superior lamina 655 and of the inferior facet surface of the superior vertebra as well as a small segment of the superior aspect of the inferior lamina 665 and of the superior facet surface of the inferior vertebra.

Figure 13:
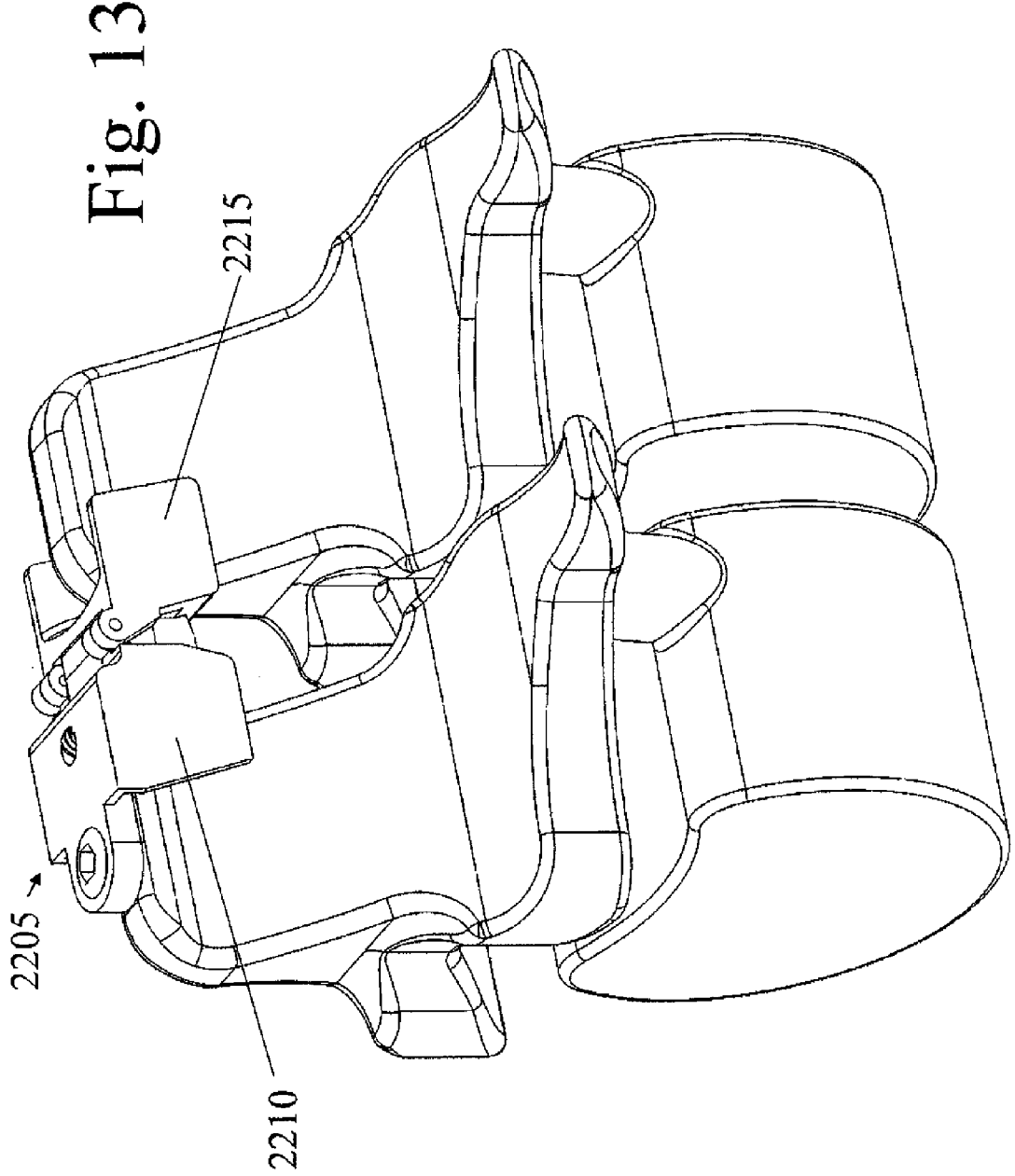
Figure 14B:
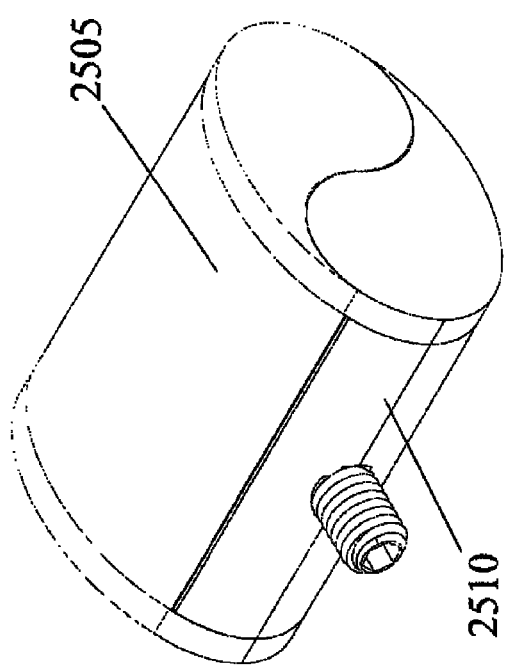
Figure 14C:
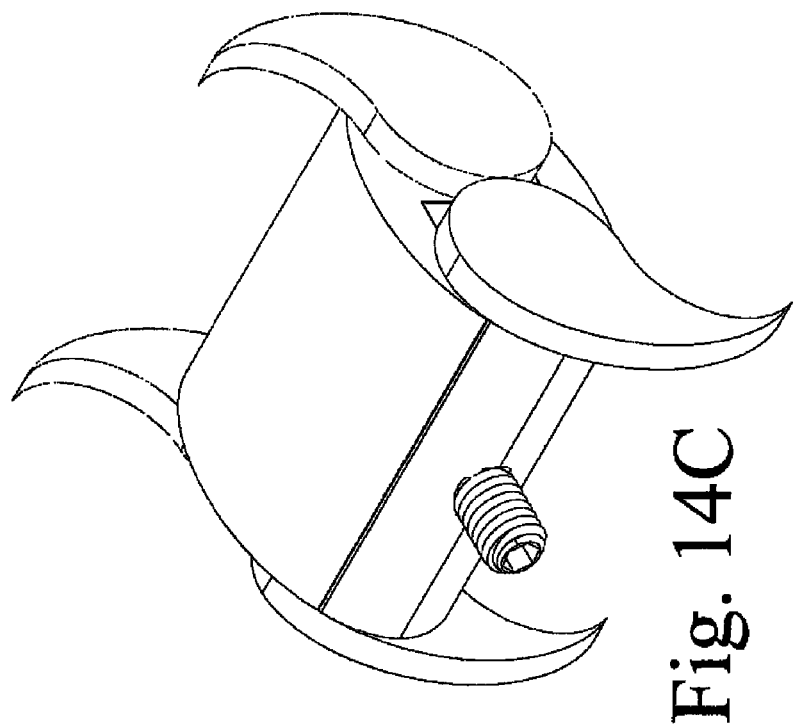
Figure 15B:
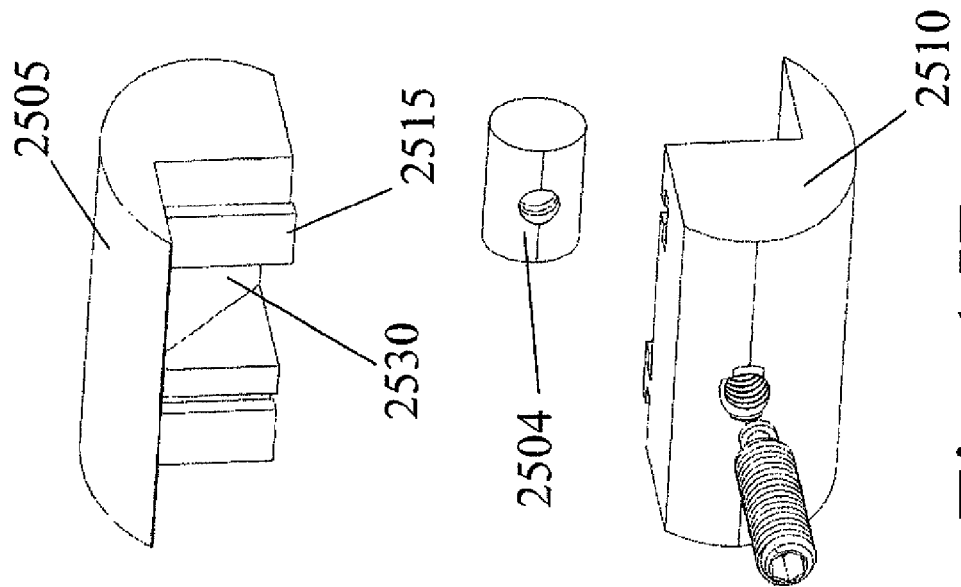
Figure 15A:
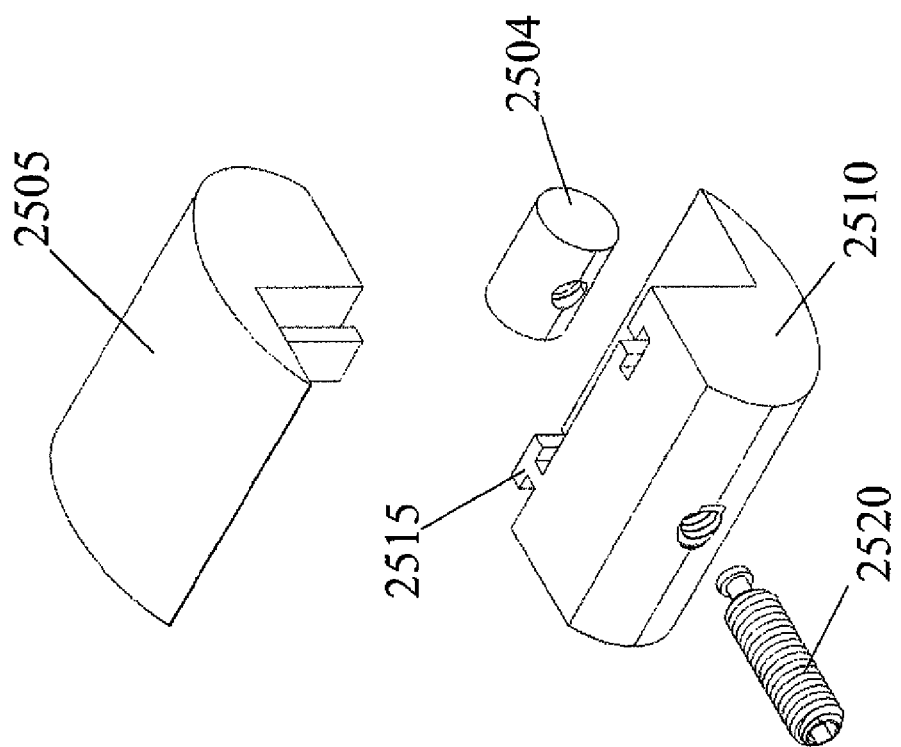

FIGS. 12 & 13 illustrate an additional embodiment wherein the implant can expand and vary in size. The device 2205 has two component members 2210 and 2215 that are joined by a joining pin 2220. Member 2210 contains threaded bore 2212 that accepts complimentary threaded screw 2214. Member 2215 has protrusion 2230 facing member 2210 and engagable by one end of threaded screw 2214. In assembly, as shown in FIG. 12A, screw 2214 is positioned within bore 2212 such that one end of the screw abuts protrusion 2230 of member 2215. With the advancement of screw 2214 relative to bore 2212, member 2215 is rotated in the direction R about the axis of joining pin 2220. In this way, the device is lengthened. In use, the device can be placed with a distractor, as previously discussed, or it can be placed into the implantation site without distraction and then expanded to the desired length. With the latter implantation technique, the implant is effectively used as the distraction device. FIG. 13 shows the implanted device.

Figure 17:
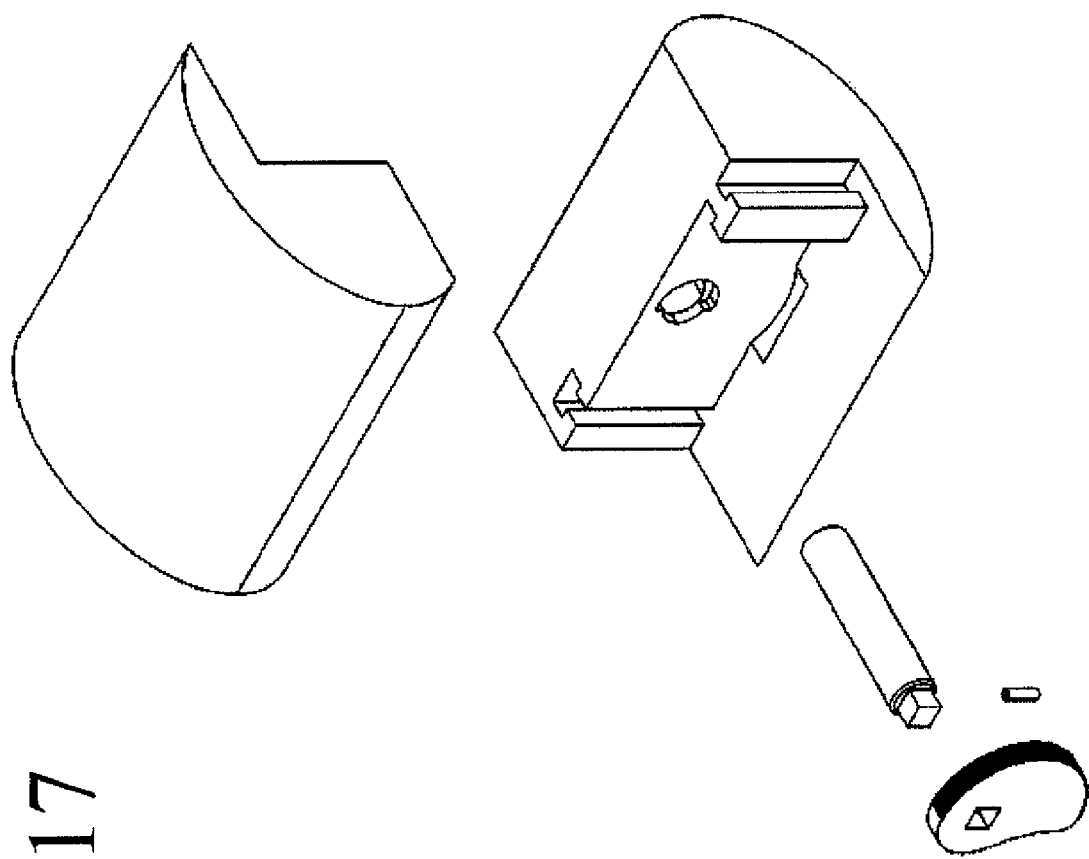
Figure 18B:
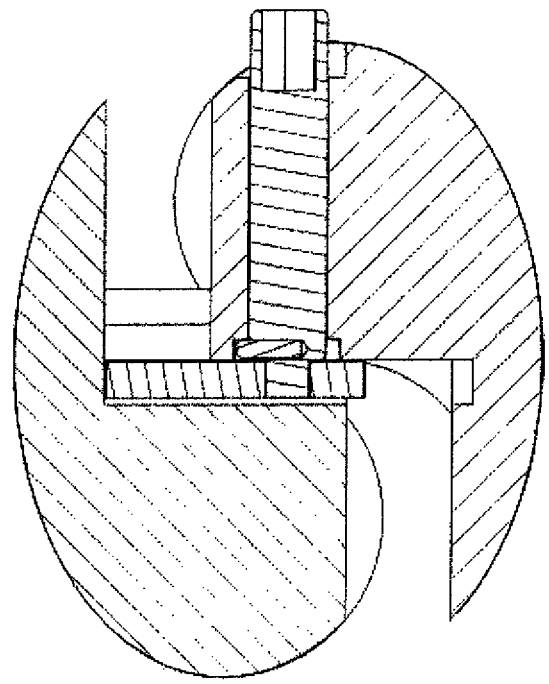
Figure 18A:
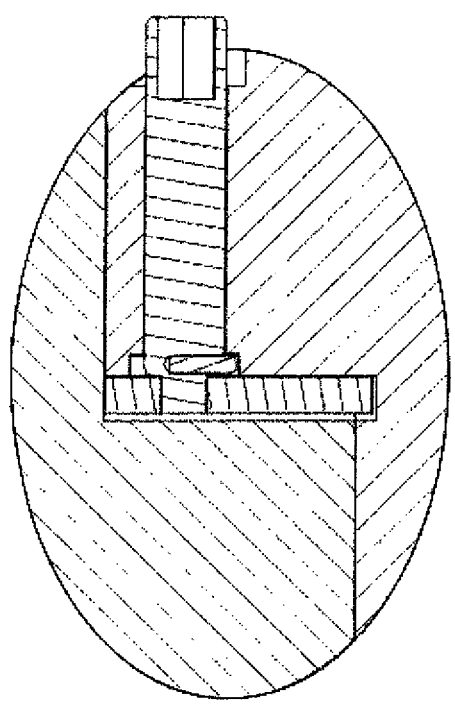

FIGS. 14 to 18 illustrate two additional mechanisms that will produce expandable implants. FIG. 14A shows the first implant mechanism. The device may be directly attached to a spinous process, as previously illustrated for other embodiments (attachment member not shown), or it may be fitted with side protrusion and then left to reside freely between two adjacent spinous processes. The latter embodiment is shown in FIG. 14B with the side protrusions closed and in FIG. 14C with side protrusions open. The component members are shown in FIGS. 15A and 15B. The device consists of two segments 2505 and 2510 that are attached by rails 2515 and complimentary cut-outs. With actuation of screw member 2520, barrel member 2524 is advance along the inclined surface 2530 of member 2505 and the device is expanded as shown in FIGS. 16A and 16B. FIG. 17 shows a cam-driven mechanism for device expansion. As illustrated in FIGS. 18A and 18B, the device expands as the actuating screw and attached cam are rotated.

Figure 20:
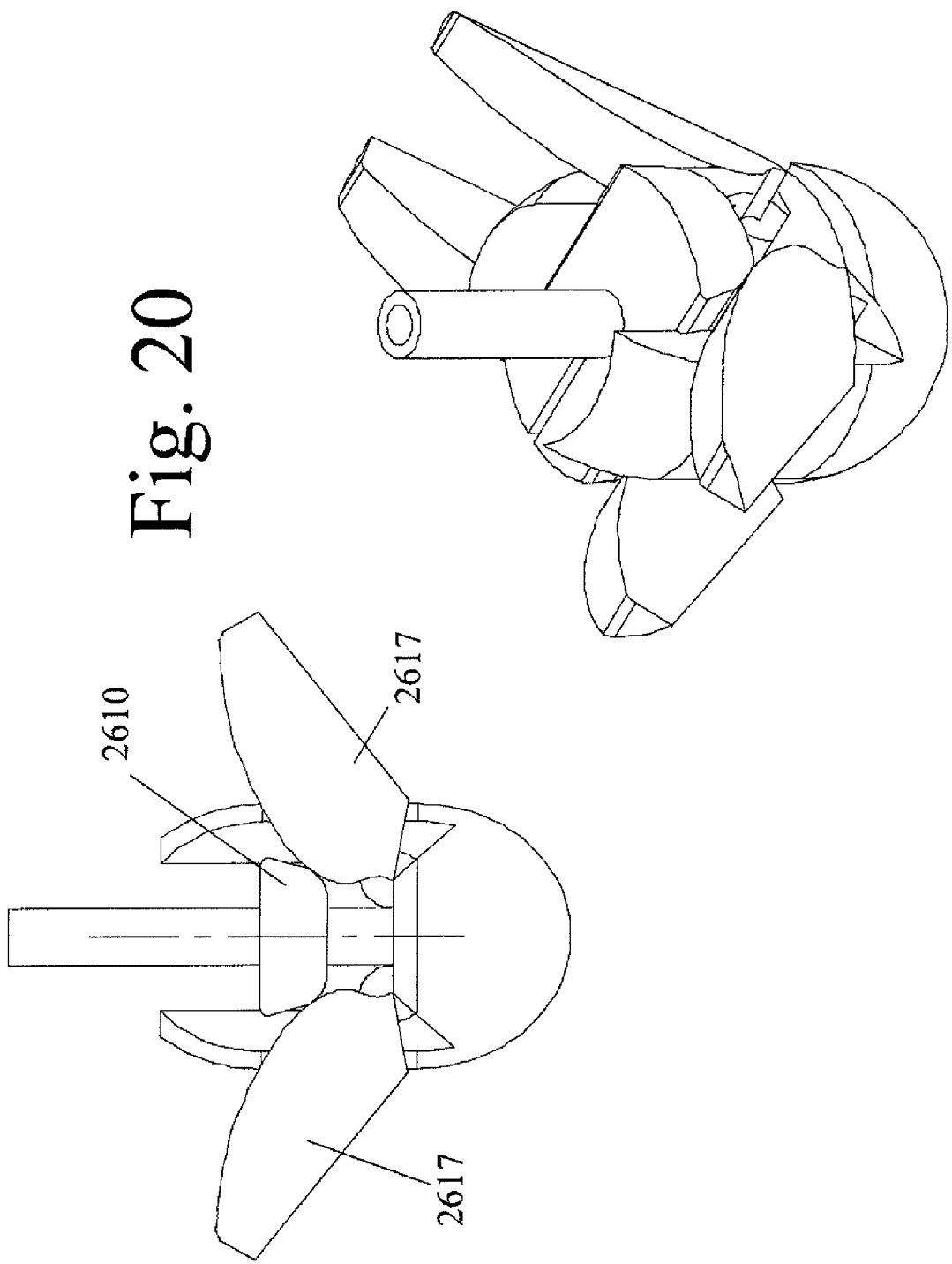
Figure 21:
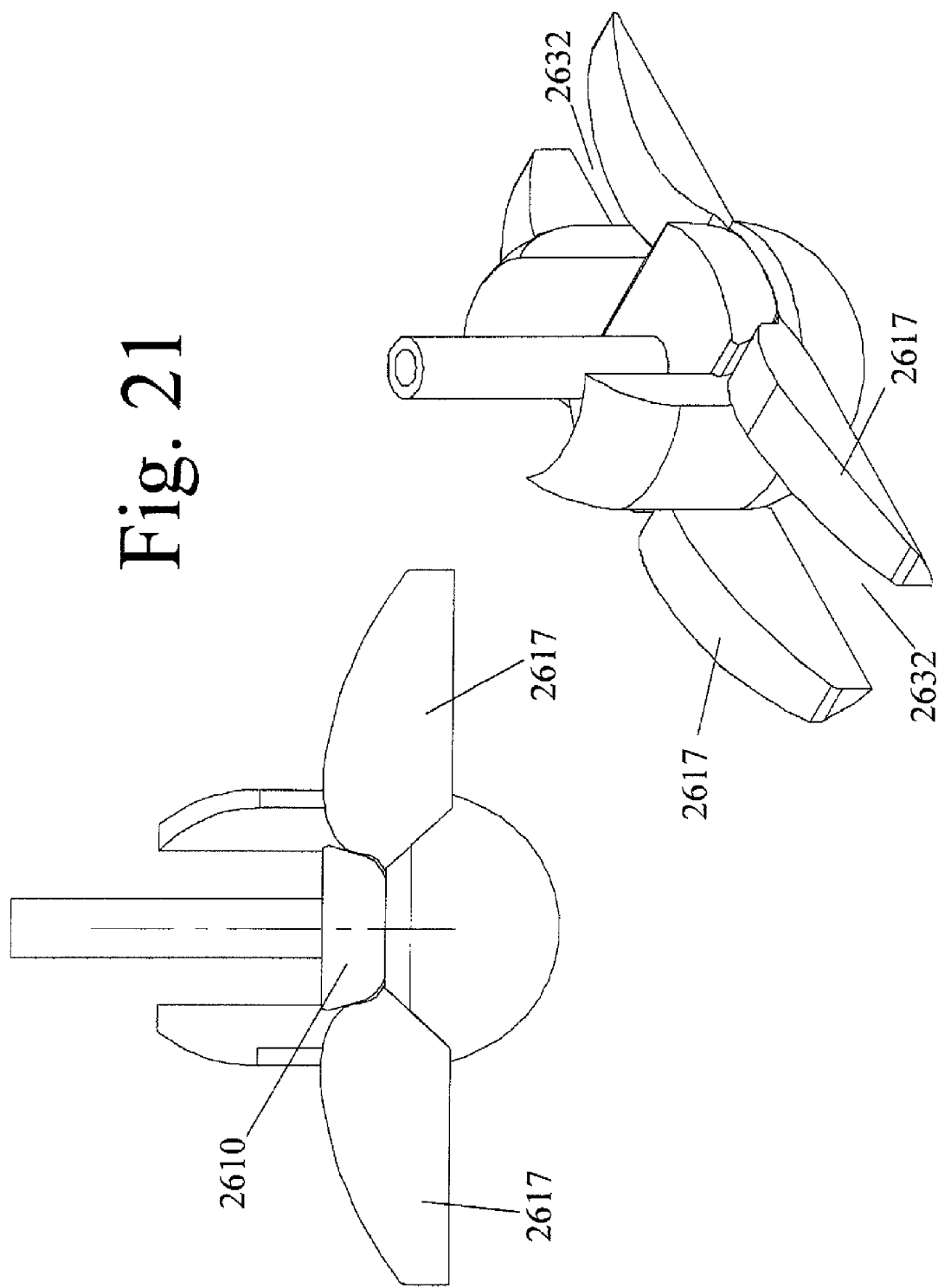

Another embodiment is shown in FIGS. 19 to 21. While the device can be configured to attach onto the spinous process as previously illustrated for other embodiments, it has expandable side members that will retain it within the interspinous space without attached to bone. Device 2605 has four side members 2617 that rotatably deploy with advancement of locking member 2610. While not illustrated, the central post 2615 has circumferentially-placed teeth or protrusions that interact with the complimentary teeth or protrusions on the outer wall of bore 2612 of locking member 2610 so as form a ratchet-like locking mechanism. As shown in FIGS. 20 and 21, side members rotate with advancement of member 2610 and the ratchet feature keeps the side members in the deployed state. In use, the device is preferably placed into the interspinous space after spinous process distraction and the side members are then opened. With deployment, each of spinous process is contained within a space 2632 between a pair of side members.

Figure 22:
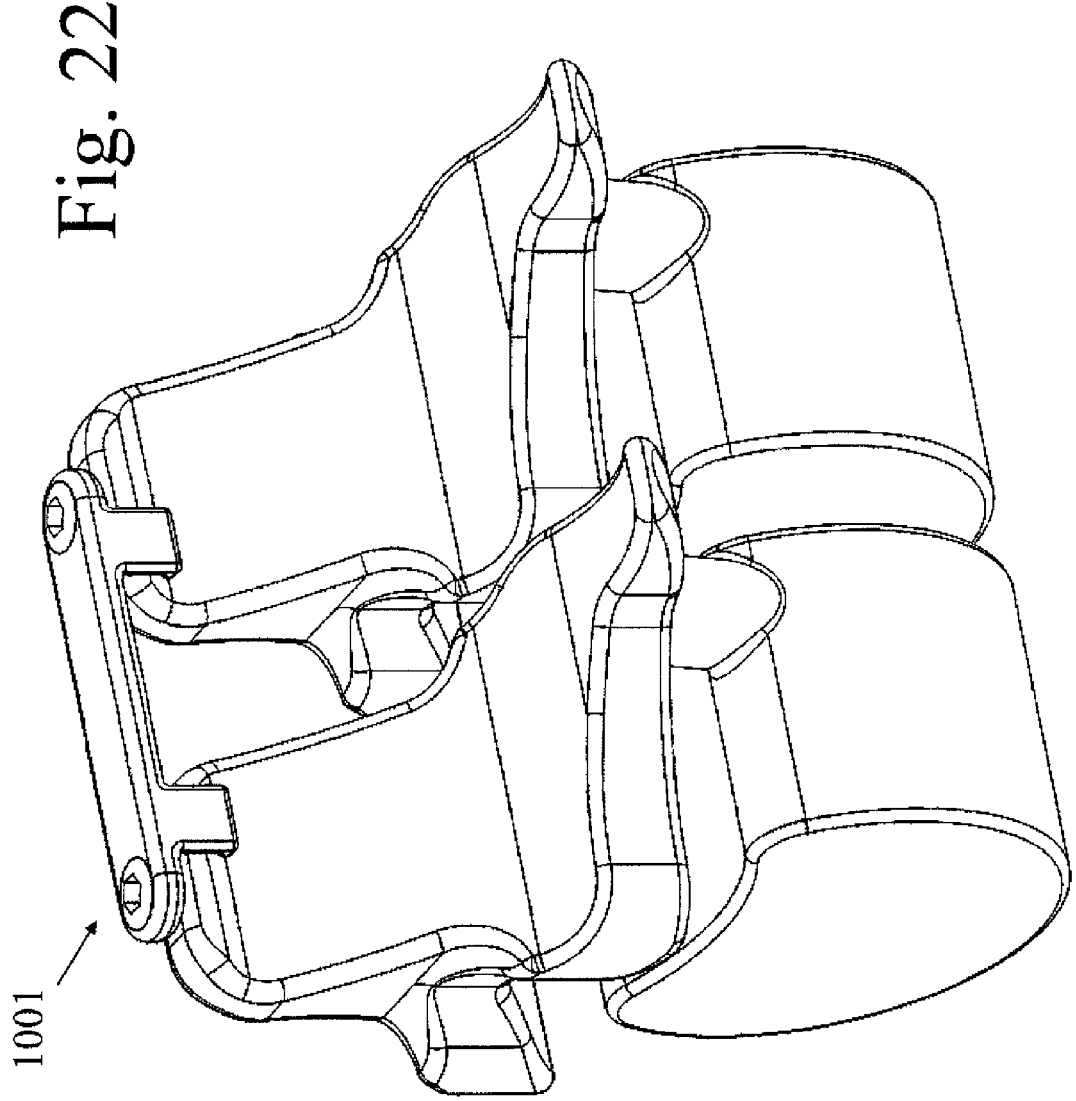
FIG. 22 shows another embodiment of an implant.
Figure 23:
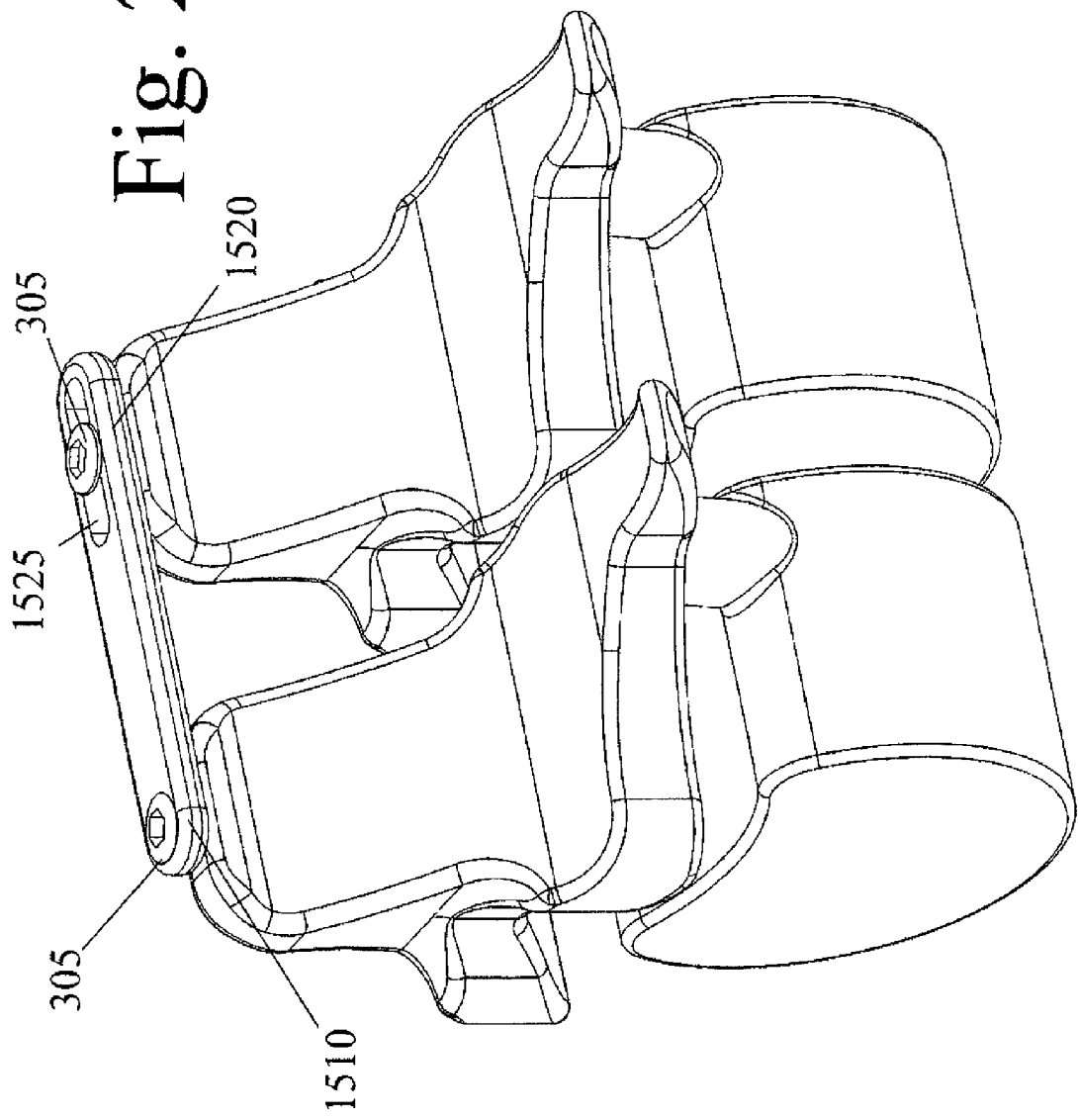
FIG. 23 shows yet another embodiment of an interspinous device.

FIGS. 22 to 27 show several embodiments that attach onto both spinous processes. In addition to limiting vertebral extension, these devices can also control the vertebral motion in anterior flexion, lateral flexion and rotation. That is, with attachment to both spinous processes, the device can be used to modulate the motion characteristics and stabilize the segment in all planes. FIG. 22 shows a rigid embodiment 1001 that can be used to immobilize the motion segment. FIG. 23 shows a dynamic device embodiment wherein an elongated member that includes a first attachment region 1510 and a second attachment region 1520. Both attachment regions include an interface for receiving a fastener such as a bone screw 305. The interface in the first attachment region 1510 is a circular borehole while the interface in the second attachment region 1520 is an elongated slot 1525. The screw 305 and the attached spinous process can move along a distance defined by the length of the slot to permit relative movement between the two spinous processes to which the device 105 is attached. The elongated slot 1525 can include or be coupled to a mechanism that permits, but elastically resists, screw movement within the slot. In this way, the vertebras are allowed to move when force is applied but they return to the neutral position when the force has dissipated.

FIG. 24 shows another embodiment of the interspinous device 105 that permits relative movement between the vertebral bodies. The device 105 includes a first attachment region 1605 and a second attachment region 1610 that are movably attached to one another via a sliding connection 1615. The first and second attachment regions can move relative to one another when a force is exerted onto the device or the attached vertebral bodies. The device may include a mechanism that biases the first and second attachment regions toward a neutral position relative to one another. When the force producing movement dissipates, the device elastically returns the vertebras to the neutral position.

FIG. 25 shows another embodiment of an interspinous device 105 that includes first and second attachment regions 1705 and 1710 that are movably attached to one another. FIG. 26A shows an exploded view of the device 105 of FIG. 25. FIG. 26B shows a cross-sectional view of the device of FIG. 25. The first and second attachment regions 1705 are movably linked to one another via a linking member 1720 that extends through a space 1905. An elastic member or material is placed on either side of bar 1910 within space 1905. The elastic member/material resists movement of the linking member 1720 to thereby resist relative movement between the first and second attachment regions 1705 and 1710. A member 1920 (such as Belleville washer) resists the movement of a head of the linking member 1720. Thus, the device is biased toward a neutral position wherein the first and second attachment regions are positioned in a predetermined location relative to one another. When the force producing movement between the first and second attachment region dissipates, the device elastically returns the vertebras to the neutral position.

FIG. 27 shows another embodiment of an interspinous device 105. The device 105 includes a first attachment region 1010 and a second attachment region 1005 that each attach to respective spinous processes of upper and lower vertebral bodies. The device 105 further includes a central region 1015 positioned between the attachment regions 1005 and 1010. The central region 1015 is positioned between the spinous processes in the implanted device. The central region is adapted to provide a range of relative movement between the first and second attachment regions. Thus, the central region can resiliently deform to provide such movement. In the illustrated embodiment, the central region 1015 includes a bellows-like structure that can alternately expand and retract to permit relative movement between the spinous processes. It is understood that one of ordinary skill in the art can fashion comparable restraining using alternative configurations that employ springs, bellows, energy absorbing materials such as rubber, urethane, fluids chambers/containers, magnets, magnetic fields and the like.

Figures 28A, 28B:
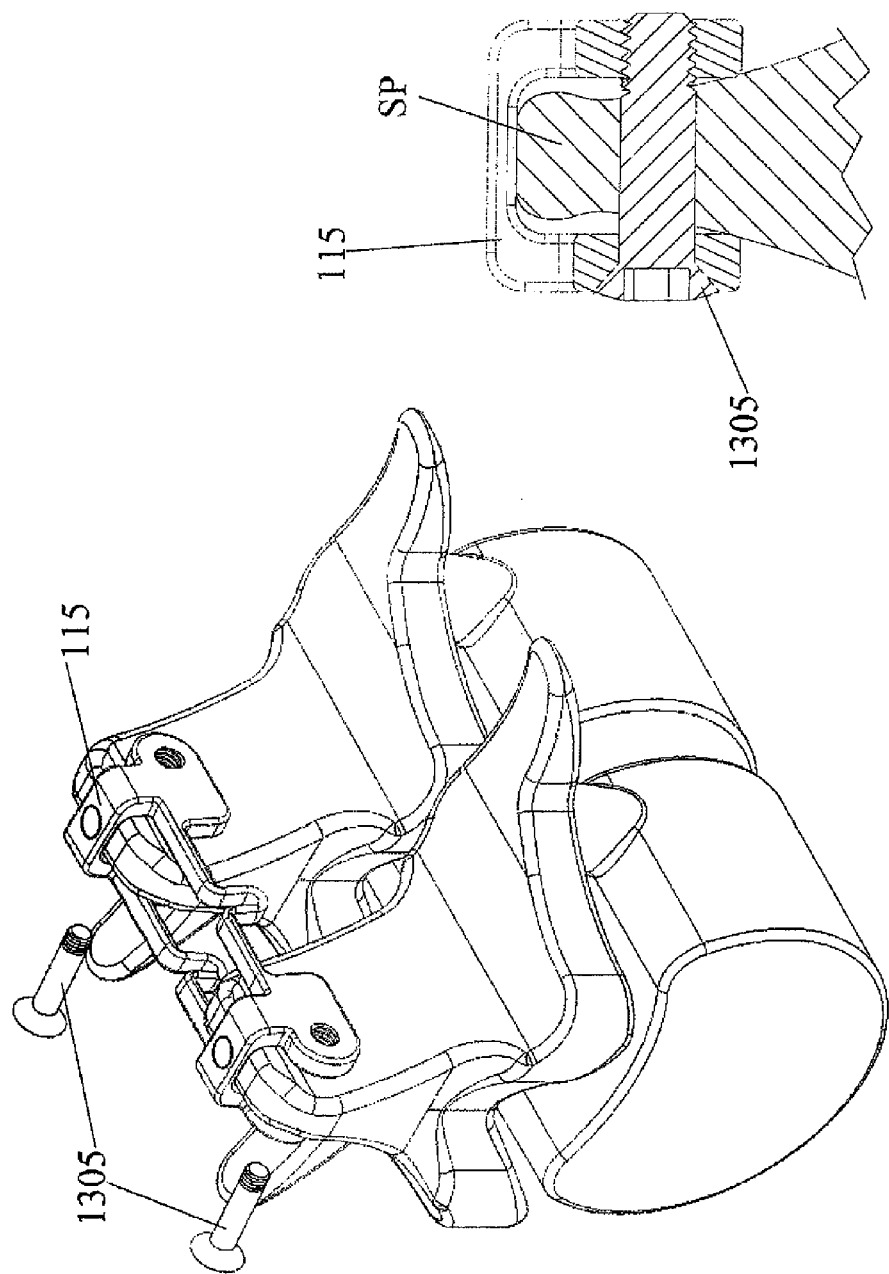
FIGS. 28A and 28B show yet another embodiment of an interspinous device.

The embodiments of the devices in FIGS. 22-27 are shown with few side flaps. However, it is understood that additional flaps that straddle the spinous processes can be readily added to these devices to provide additional stability. In addition, the bone fasteners may be placed in others segments of the spinous process or attach onto the lamia on either side of the spinous processes. FIG. 28A shows an additional embodiment where screws or similar fasteners may be additionally attached onto the sides of the spinous processes. FIG. 28B shows a cross-sectional view of a bone screw 1305 extending through the side of a spinous process SP. The device 105 of FIGS. 28A and 28B include attachment sections 115 having upper walls and flaps that extend downwardly to provide a substantial "U" shape that fits over the spinous process. As shown, section 115 may also have an additional bore for screw placement along the long axis of the spinous process.

Figure 29:
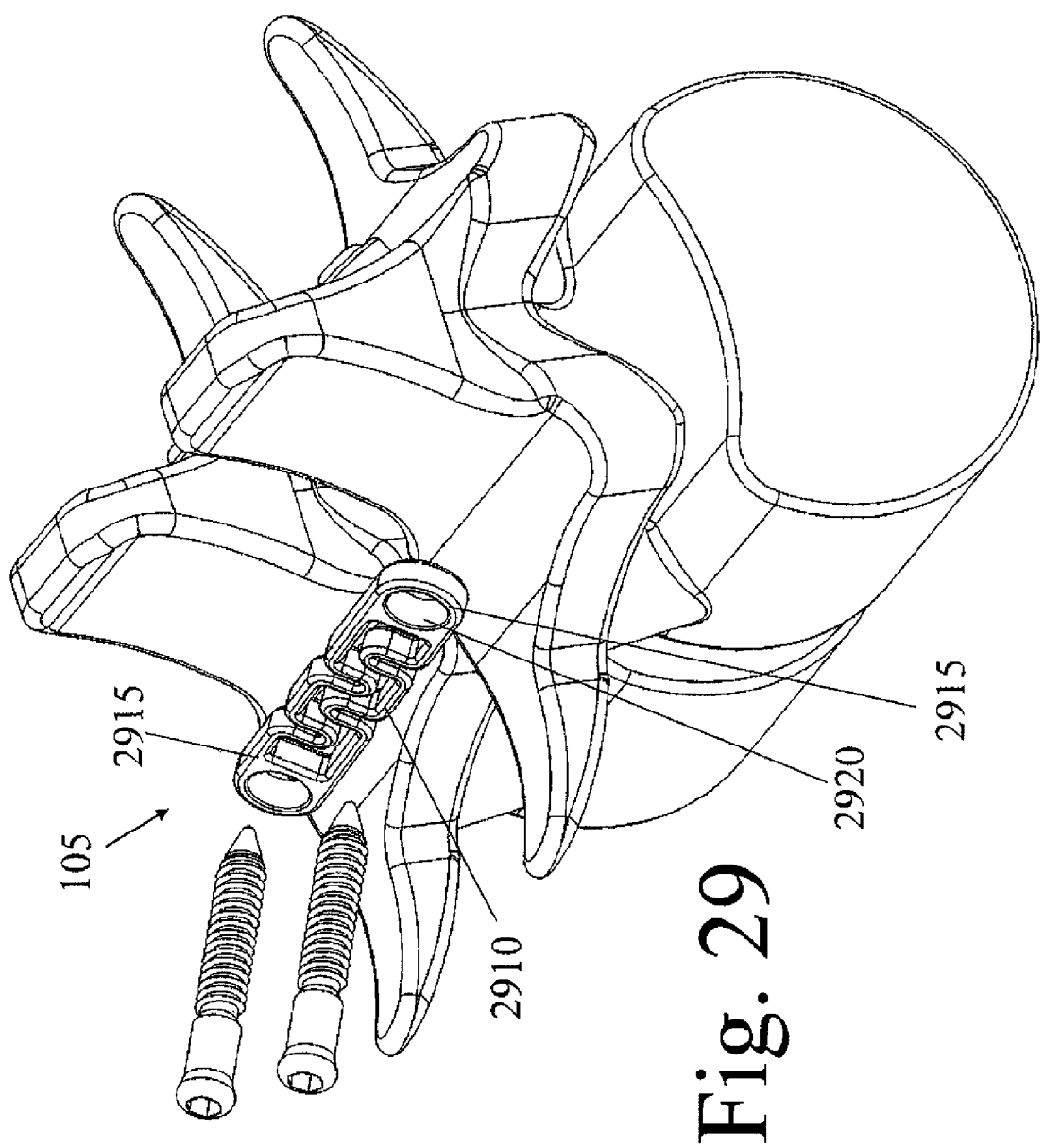
FIG. 29 shows yet another embodiment of an interspinous device.

In FIGS. 29 to 32 additional methods of device fixation onto bone are illustrated. FIG. 29 shows another embodiment of an interspinous device 105. The device includes a malleable central region 2910 positioned between a pair of attachment regions 2915. The attachment regions 2915 include boreholes 2920 that receive bone screws. The bone screws can be fixated in the laminal segment of an underlying vertebral body. The central region 2910 is malleable and can take on other shapes to permit movement between the attached vertebral bodies. FIG. 30A shows cross-sectional view of two devices of FIG. 29 attached to bone. In FIG. 30B, the screw trajectory extends along the axis of the spinous process. In FIG. 30A, the screw trajectory extends along the axis of lamia bone and is contrasted to the trajectory of the spinous process screws (of prior embodiments) that is shown in FIG. 30B.

The placement of the device of FIG. 29 can be performed as a minimally invasive surgical procedure. The spinous processes of the operative level are identified and a skin incision is made between them. The soft tissue is dissected off of the side of the spinous process to which the interspinous device is to be attached. The device is then placed through the incision into the depth of the wound and onto the side of the spinous process. Percutaneous placement of the lamina screw is then performed. The screw is placed through a stab wound in the skin, across the underlying soft tissue, through one of the device's bore holes and into the underlying lamina.

Figures 31A, 31B:
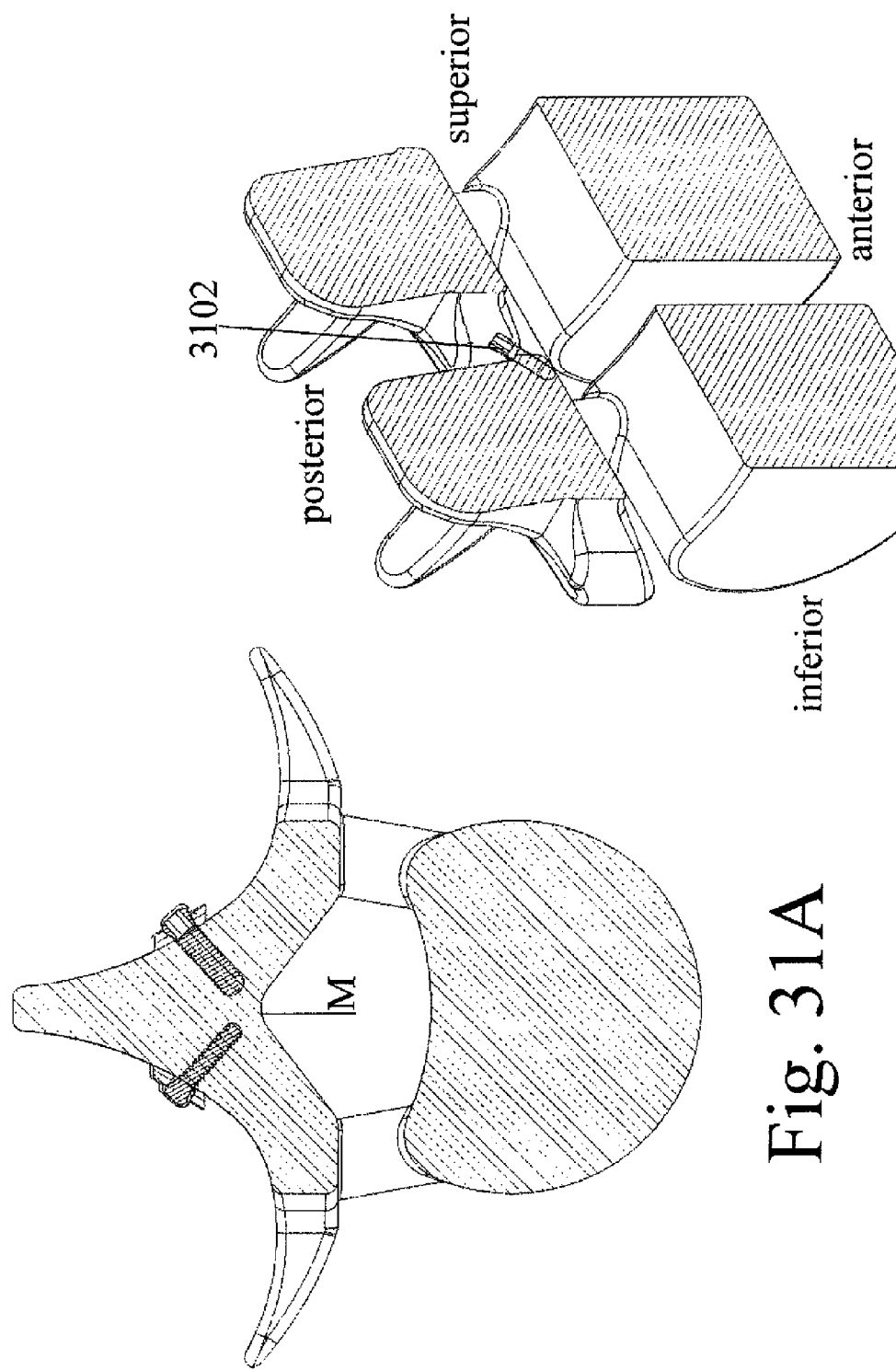
Figure 32:
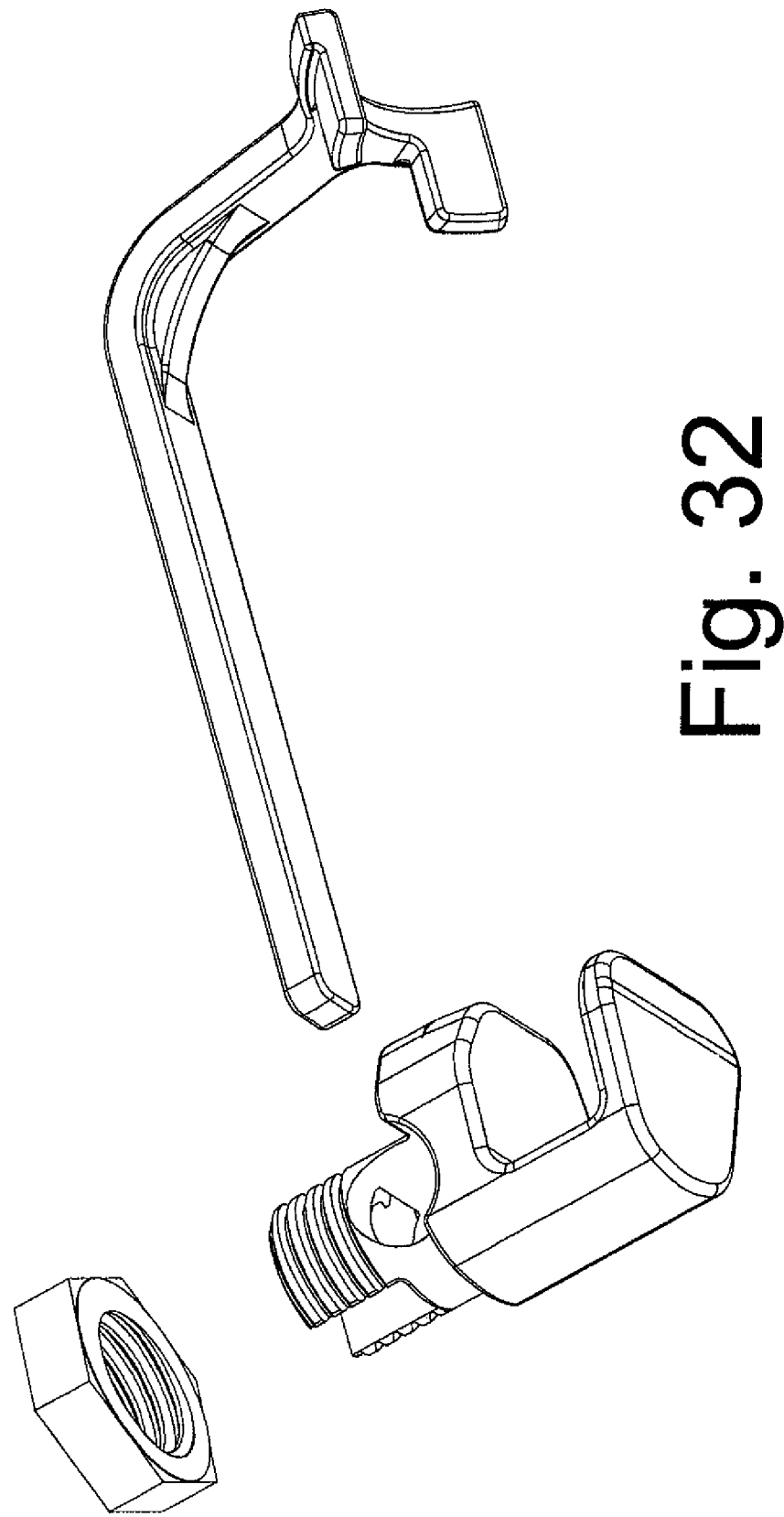
FIG. 32 shows a bone clamp that can be used to clamp the superior and inferior surface of the lamina on each side of the spinous process.

Additional screw trajectories are illustrated in FIG. 31. Unlike the lamina screw of FIG. 30A, the screw trajectory of FIG. 31A preferably aims the screw tip towards the vertebral midline M. In FIG. 31B, screw 3102 is anchored into the midline of the anterior lip of the superior aspect of the spinous process. This segment of bone is particularly strong and well situated for fastener placement. FIG. 32 illustrates a bone clamp that can be used to clamp the superior and inferior surface of the lamina on each side of the spinous process. The preceding attachment methods can be adapted for use with any of the illustrated embodiments.

Figure 33B:
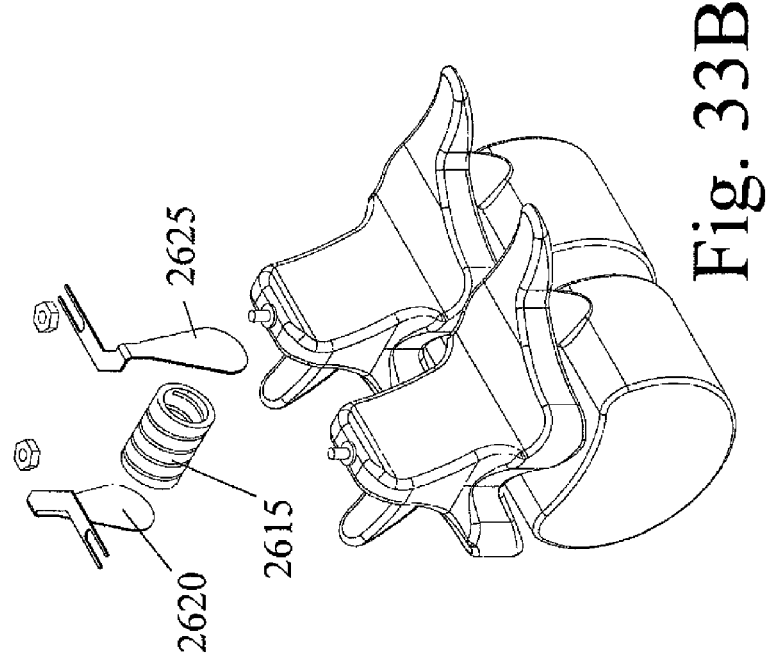
FIGS. 33A and 33B show another embodiment of an interspinous device.
Figure 33A:
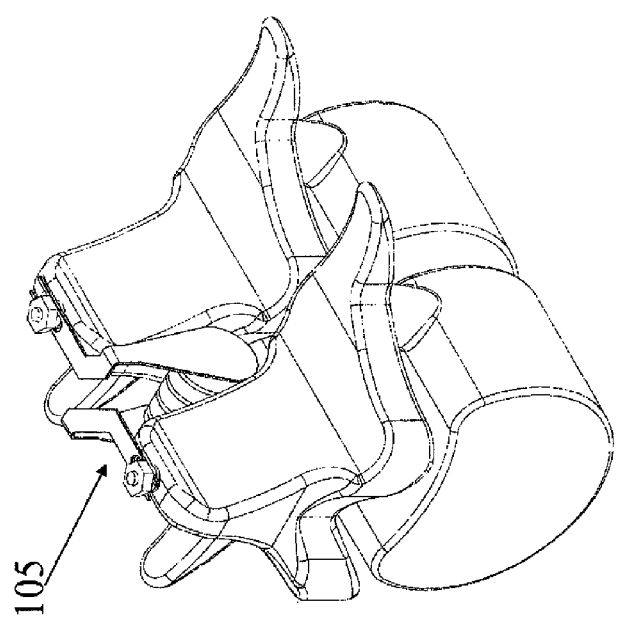

FIGS. 33A and 33B show yet another embodiment of an interspinous device 105. The device 105 includes a malleable central region 2615 attached to a pair of attachment regions 2620 and 2625. The attachment regions are attached to a pair of screws 305 that are attached the spinous processes. The central region 2615 limits the extent of vertebral extension at the implanted level. The malleable nature of the device resists vertebral extension and rotation. The device also resists anterior or posterior displacement of one vertebral level relative to the other. While depicted as being comprised of three separate members for illustration, device 105 is preferably manufactured and used as a single unit. The central region 2615 comprises a spring-like structure formed of an elongated member that has a coiled configuration. The ends of the elongated members are attached to the spinous processes. The central region extends along an axis that is oriented between the spinous processes.

Any of the device embodiments can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineriized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, the outer surface of the bone screw assemblies may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the screw assemblies, interconnectors and/or any component can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An orthopedic device configured to be at least partially implanted within an inter-spinous space, said inter-spinous space being bordered by at least a superior spinous process and an inferior spinous process, said orthopedic device comprising:
    a first longitudinal member having a length greater than a distance from an inferior end of said superior spinous process to a superior end of said inferior spinous process;
    a second longitudinal member substantially aligned to face said first longitudinal member and having a length greater than said distance;
    a transverse member configured to integrally diverge from said first longitudinal member, said transverse member extending towards and at least contacting said second longitudinal member; and
    a cavity at least partially bounded by said first longitudinal member and said transverse member, said cavity housing a bone forming material and configured to open directly onto one of said spinous processes;
    at least one rigid bone fixation member that extends from one of said longitudinal members and fixates onto one of said spinous processes;
    wherein at least said first and second longitudinal members and said transverse member are formed by a non-osteogenic material.

2. The orthopedic device of claim 1, wherein at least one external surface of said orthopedic device is textured in order to promote fixation onto an adjacent bone.

3. The orthopedic device of claim 1, wherein said orthopedic device is at least partially comprised of titanium.

4. The orthopedic device of claim 1, wherein said orthopedic device is at least partially comprised of a plastic material.

5. An orthopedic device configured to be positioned at least partially within an inter-spinous space, said inter-spinous space being bordered at least by a superior spinous process and an inferior spinous process, said orthopedic implant comprising:
    a first longitudinal member having a length greater than a distance from an inferior end of said superior spinous process to a superior end of said inferior spinous process;
    a second longitudinal member substantially aligned to face said first longitudinal member and having a length greater than said distance; and
    a first and a second transverse member configured to integrally diverge from said first longitudinal member, said first and second transverse members being comprised of a non-osteoinductive material, and being substantially aligned to face one another and to define a cavity therebetween, said cavity housing a bone forming material and configured to open directly onto one of said spinous processes; and
    at least one rigid bone fixation member that extends from one of said longitudinal members and fixates onto one of said spinous processes.

6. The orthopedic device of claim 5, wherein at least one external surface of said orthopedic device is textured in order to promote fixation onto an adjacent bone.

7. The orthopedic device of claim 5, wherein said orthopedic device is at least partially comprised of titanium.

8. The orthopedic device of claim 5, wherein said orthopedic device is at least partially comprised of a plastic material.

9. A method for placement of an orthopedic device within an inter-spinous space, said inter-spinous space being bordered at least by a superior spinous process and an inferior spinous process, comprising:
    decorticating a bony surface of at least a portion of at least one of said spinous processes;
    placing a first longitudinal member of said orthopedic device having a length greater than a distance from an inferior end of said superior spinous process to a superior end of said inferior spinous process, such that it abuts a superior aspect of said inferior spinous process;
    placing a second longitudinal member of said orthopedic device having a length greater than said distance such that it substantially faces said first longitudinal member;
    positioning a cavity of said orthopedic device at least partially within said inter-spinous space, said cavity formed between said first longitudinal member and a transverse member of said orthopedic device that extends from said first longitudinal member and towards said second longitudinal member, said cavity housing a bone forming material therein; and
    aligning an opening of said cavity to contact said decorticated bony surface;
    wherein at least one rigid bone fixation member extends from a longitudinal member and fixates onto one of said spinous processes; and
    wherein at least said first and second longitudinal members and said transverse member are formed by a non-osteogenic material.

10. The method of claim 9, further comprising causing at least one external surface of said orthopedic device to be textured in order to fixate onto an adjacent bone.

11. The method of claim 9, further comprising causing at least a portion of said orthopedic device to be manufactured from a metallic material.

12. The method of claim 9, further comprising causing at least a portion of said orthopedic device to be manufactured from a plastic material.

* * * * *